US010760093B2

(12) United States Patent
Millet et al.

(10) Patent No.: US 10,760,093 B2
(45) Date of Patent: Sep. 1, 2020

(54) RESISTANCE TO RUST DISEASE IN WHEAT

(71) Applicant: Technology Innovation Momentum Fund (Israel) Limited Partnership, Tel Aviv (IL)

(72) Inventors: Eitan Millet, Beit Elazari (IL); Jacob Manisterski, Petach Tiqva (IL); Pnina Ben-Yehuda, Kfar Saba (IL)

(73) Assignee: TECHNOLOGY INNOVATION MOMENTUM FUND (ISRAEL) LIMITED PARTNERSHIP, Tel-Aviv (IL)

( * ) Notice: Subject to any disclaimer, the term of this patent is extended or adjusted under 35 U.S.C. 154(b) by 190 days.

(21) Appl. No.: 15/021,330

(22) PCT Filed: Sep. 10, 2014

(86) PCT No.: PCT/IL2014/050804
§ 371 (c)(1),
(2) Date: Mar. 11, 2016

(87) PCT Pub. No.: WO2015/036995
PCT Pub. Date: Mar. 19, 2015

(65) Prior Publication Data
US 2016/0222406 A1    Aug. 4, 2016

Related U.S. Application Data

(60) Provisional application No. 61/876,240, filed on Sep. 11, 2013.

(51) Int. Cl.
A01H 5/10 (2018.01)
A01H 1/04 (2006.01)
C12N 15/82 (2006.01)
C12Q 1/6895 (2018.01)

(52) U.S. Cl.
CPC .......... C12N 15/8282 (2013.01); A01H 1/04 (2013.01); A01H 5/10 (2013.01); C12Q 1/6895 (2013.01); C12Q 2600/13 (2013.01)

(58) Field of Classification Search
CPC .. A01H 5/10; C12N 15/8282; C12N 15/8261; C12N 5/14; C12Q 2600/156
See application file for complete search history.

(56) References Cited

FOREIGN PATENT DOCUMENTS

| CN | 101760459 | 6/2010 |
|----|-----------|--------|
| WO | 9529238 A1 | 11/1995 |
| WO | 9945118 A1 | 9/1999 |
| WO | 2013082335 A1 | 6/2013 |

OTHER PUBLICATIONS

Marais, G. F., B. McCallum, and A. S. Marais. "Leaf rust and stripe rust resistance genes derived from Aegilops sharonensis." Euphytica 149.3 (2006): 373-380.*
Olivera, P. D., et al. "Development of a genetic linkage map for Sharon goatgrass (Aegilops sharonensis) and mapping of a leaf rust resistance gene." Genome 56.7 (2013): 367-376.*
Olivera, P. D., et al. "Genetics of resistance to wheat leaf rust, stem rust, and powdery mildew in Aegilops sharonensis." Phytopathology 98.3 (2008): 353-358. (Year: 2008).*
Olivera, P. D., et al. "Development of a genetic linkage map for Sharon goatgrass (Aegilops sharonensis) and mapping of a leaf rust resistance gene." Genome 56.7 (2013): 367-376. (Year: 2013).*
Collard, B. C. Y., et al. "An introduction to markers, quantitative trait loci (QTL) mapping and marker-assisted selection for crop improvement: the basic concepts." Euphytica 142.1-2 (2005): 169-196. (Year: 2005).*
Marais, G. F., B. McCallum, and A. S. Marais. "Leaf rust and stripe rust resistance genes derived from Aegilops sharonensis." Euphytica 149.3 (2006): 373-380. (Year: 2006).*
Anikster et at., "Resistance to Leaf Rust, Stripe Rust, and Stem Rust in *Aegilops* spp. in Israel". Plant Disease 89: 303-308 (2005).
Brenchley et al., "Analysis of the bread wheat genome using whole-genome shotgun sequencing". Nature 491 (7426): 705-10 (2012).
Champouret et al., "A pipeline for cloning resistance genes effective against African Puccinia graminis tritici races from the diploid wheat relative Aegilops sharonensis". Proceedings Borlaug Global Rust Initiative 2012 Technical Workshop, Sep. 1-4 Beijing, China; 66-74 (2012).
Chen "Epidemiology and control of stripe rust [*Puccinia striiformis* f. sp. tritici] on wheat". Can J Plant Pathol 27: 314-337 (2005).
Chen et al., "Inheritance of stripe rust resistance in wheat cultivars used to differentiate races of Puccinia striiformis in North America". Phytopathology 82: 633-637 (1992).
Chen et al., "Virulence races of *Puccinia striiformis* f. sp. tritici in 2006 and 2007 and development of wheat stripe rust and distributions, dynamics, and evolutionary relationships of races from 2000 to 2007 in the United States". Can J Plant Pathol 32: 315-333(2010).
Doyle et al "A rapid DNA isolation procedure for small quantities of fresh leaf tissue". Phytochemical Bulletin 19: 11-15(1987).
Endo "Two types of gametocidal chromosome of Aegilops sharonensis and Ae". longissima. Jpn J Genet 60: 125-135 (1985).
Feldman "Gene transfer from wild species into cultivated plants". Acta Biol Yugoslav Genet 15: 145-161(1983).

(Continued)

Primary Examiner — Weihua Fan
(74) Attorney, Agent, or Firm — Browdy and Neimark, PLLC

(57) ABSTRACT

The present invention provides wheat cultivars that are resistant to leaf rust and/or stripe rust disease caused by strains of the fungus Puccinia and to means and methods for producing same. Particularly, the present invention provides wheat cultivars comprising a chromosome segment of Ae. sharonensis, the chromosome segment confers, enhances, or otherwise facilitates resistance of the wheat plants to leaf rust and/or stripe rust disease.

17 Claims, 11 Drawing Sheets
Specification includes a Sequence Listing.

(56) References Cited

OTHER PUBLICATIONS

Friebe et al., "Characterization of a knock-out mutation at the Gc2 locus in wheat". Chromosoma 111(8): 509-17 (2003).
International Barley Genome Sequencing Consortium et al., "A physical, genetic and functional sequence assembly of the barley genome". Nature 491(7426): 711-6(2012).
Jia et al., "Aegilops tauschii draft genome sequence reveals a gene repertoire for wheat adaptation". Nature 496 (7443): 91-5(2013).
Line et al "Virulence, aggressiveness, evolution, and distribution of races of Puccinia striiformis (the cause of stripe rust of wheat) in North America 1968-1987". US Department of Agriculture Technical Bulletin No. 1788,44 (1992).
Long et al "A north American system of nomenclature for *Puccinia recondite* f. sp. Tritici". Phytopathology 79: 525-529 (1989).
Maan "Exclusive Preferential Transmission of an Alien Chromosome in Common Wheat". Crop Sci 15: 287-292 (1975).
Marais et al., "Transfer of rust resistance genes from *Triticum* species to common wheat". S Afr J Plant Soil 20: 193-198 (2003).
Marais et al.,"Leaf rust and stripe rust resistance genes derived from Aegilops sharonensis". Euphytica 149: 373-380 (2006).
Marais et al., "Reduction of Aegilops sharonensis chromatin associated with resistance genes Lr56 and Yr38 in wheat". Euphytica 171: 15-22 (2010).
Mascher et al., "Barley whole exome capture: a tool for genomic research in the genus *Hordeum* and beyond". Plant J 76(3): 494-505 (2013).
Millet "Exploitation of *Aegilops* species of section Sitopsis for wheat improvement". Isr. J Plant Sci 55: 277-287 (2007).
Millet et al., "Distribution of Sharon goat grass (*Aegilops sharonensis* Eig) in Israel". Isr J Plant Sci 54: 243-248 (2006).
Millet et al., "Introgression of leaf rust and stripe rust resistance from Sharon goatgrass (*Aegilops sharonensis* Eig) into bread wheat (Triticum aestivum L.)". Genome 57(6): 309-16 (2014).
Milus et al., "Aggressiveness of *Puccinia striiformis* f. sp. tritici isolates in south-central United States". Plant Dis 90: 847-852 (2006).
Olivera et al., "Aegilops sharonensis: Origin, genetics, diversity, and potential for wheat improvement. Botany" 87(8): 740-756 (2009).
Olivera et al., "Resistance of Sharon Goatgrass (*Aegilops sharonensis*) to fungal diseases of wheat". Plant Dis 91: 942-950(2007).
Olivera et al., "Genetics of resistance to wheat leaf rust, stem rust, and powdery mildew in Aegilops sharonensis". Phytopathology 98: 353-358 (2008).
Olivera et al., "Development of a genetic linkage map for Sharon goatgrass (*Aegilops sharonensis*) and mapping of a leaf rust resistance gene". Genome 56(7): 367-376 (2013).
Potrykus "Gene Transfer to Plants: Assessment of Published Approaches and Results". Annual Review of Plant Physiology and Plant Molecular Biology 42: 205-225 (1991).
Qi et al., "Homoeologous recombination, chromosome engineering and crop improvement". Chromosome Res 15: 3-19 (2007).
Schneeberger et al., "SHOREmap: simultaneous mapping and mutation identification by deep sequencing". Nat Methods 6(8): 550-1 (2009).
Shimamoto et al., "Fertile transgenic rice plants regenerated from transformed protoplasts". Nature 338: 274-276 (1989).
The International Brachypodium Initiative "Genome sequencing and analysis of the model grass Brachypodium distachyon". Nature 463: 763-768 (2010).
Voorrips "MapChart: Software for the graphical presentation of linkage maps and QTLs". J Hered 93: 77-78 (2002).
Zhang et al., "Comparative genetic analysis of the Aegilops longissima and Ag. sharonensis genomes with common wheat". Theor Appl Genet 103: 518-525 (2001).
Gupta et al., "Development and validation of molecular markers linked to an Aegilops umbellulata—derived leaf-rust-resistance gene, Lr9, for marker-assisted selection in bread wheat" Genome, 48(5): 823-830 (2005).
Olson et al., "Introgression of stem rust resistance genes SrTA10187 and SrTA10171 from Aegilops tauschii to wheat" Theoretical and applied genetics, 126(10):2477-2484 (2013).
Jaccoud et al., Diversity arrays: a solid state technology for sequence information independent genotyping, Nucleic Acids Research, 29(4e25):1-7 (2001).
Yu et al., Discovery and characterization of two new stem rust resistance genes in Aegilops sharonensis, Theor Appl Genet, 130:1207-1222 (2017).
Kilian et al., Chapter 1: Aegilops, In: Wild Crop Relatives: Genomic and Breeding Resources, Cereals, pp. 1-74 (2011).
Millet et al., Genome Targeted Introgression of Resistance to African Stem Rust from Aegilops sharonensis into Bread Wheat, the Plant Genome, 10(3):1-11 (2017).
Millet et al., Exploitation of Wild Cereals for Wheat Improvement in the Institute for Cereal Crops Improvement, CAB International, pp. 554-563 (2007).

* cited by examiner

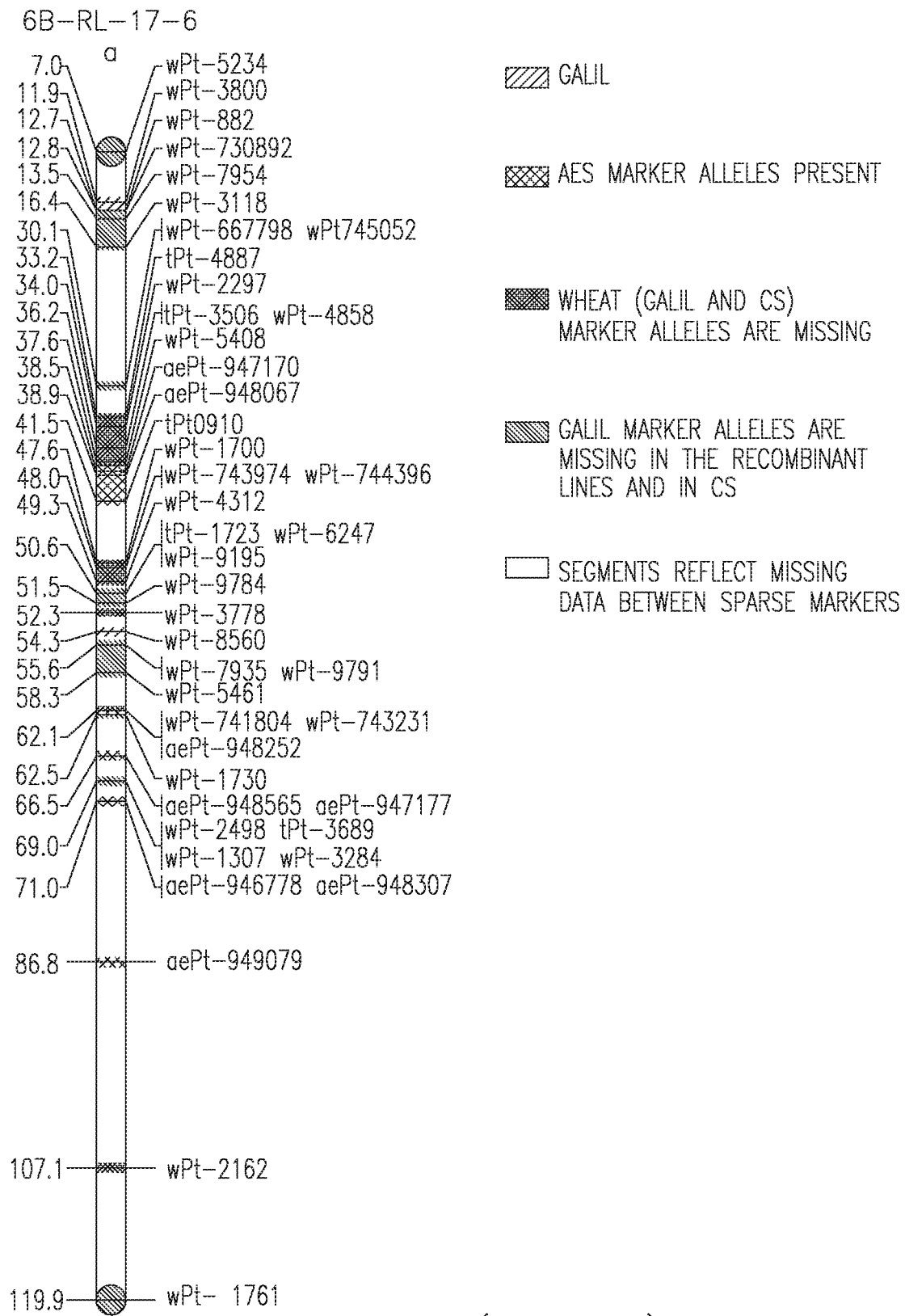
FIG 2 (cont. 1)

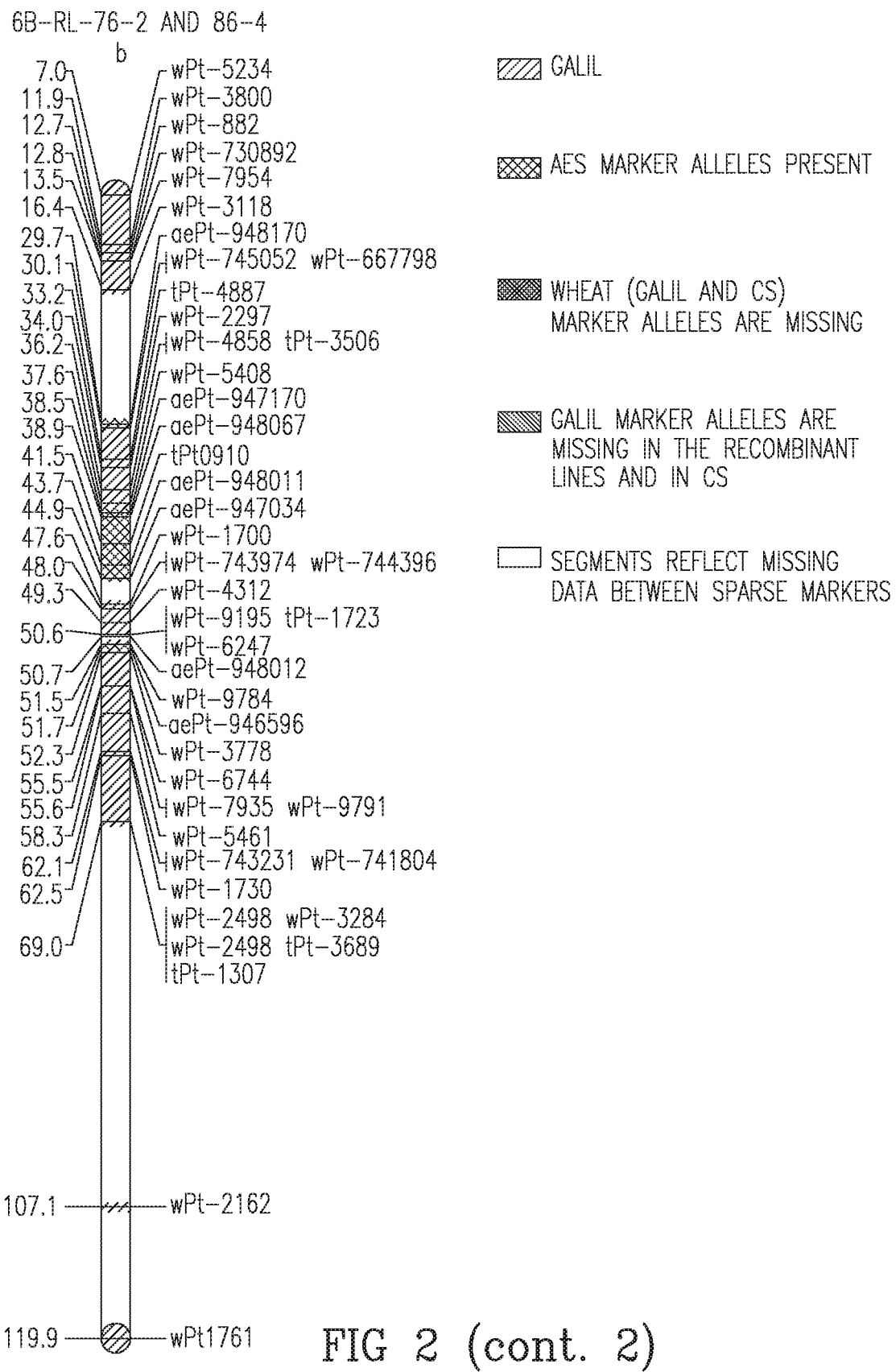
FIG 2 (cont. 2)

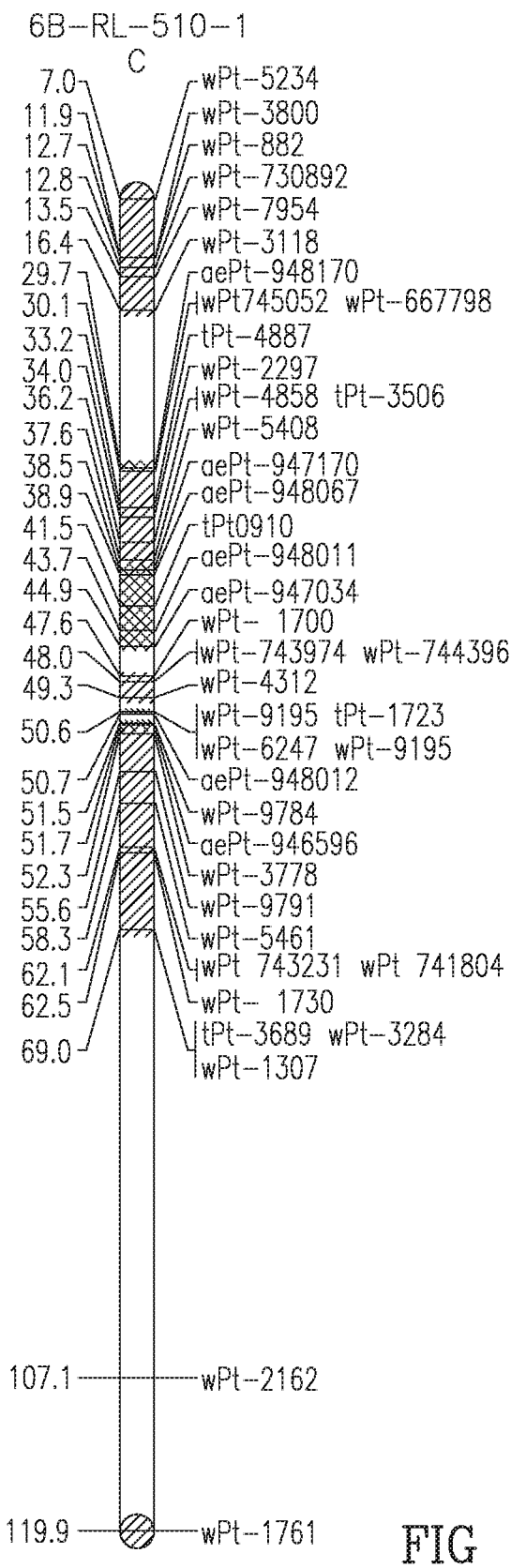
FIG 2 (cont. 3)

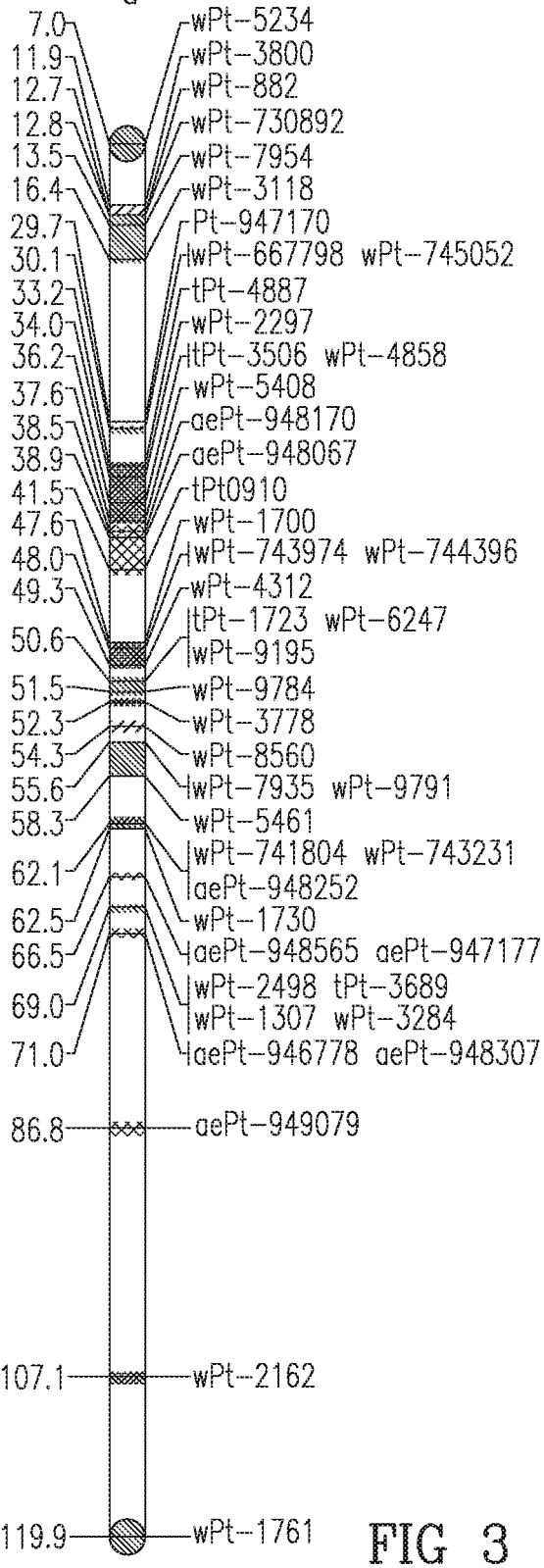
FIG 3 (cont. 1)

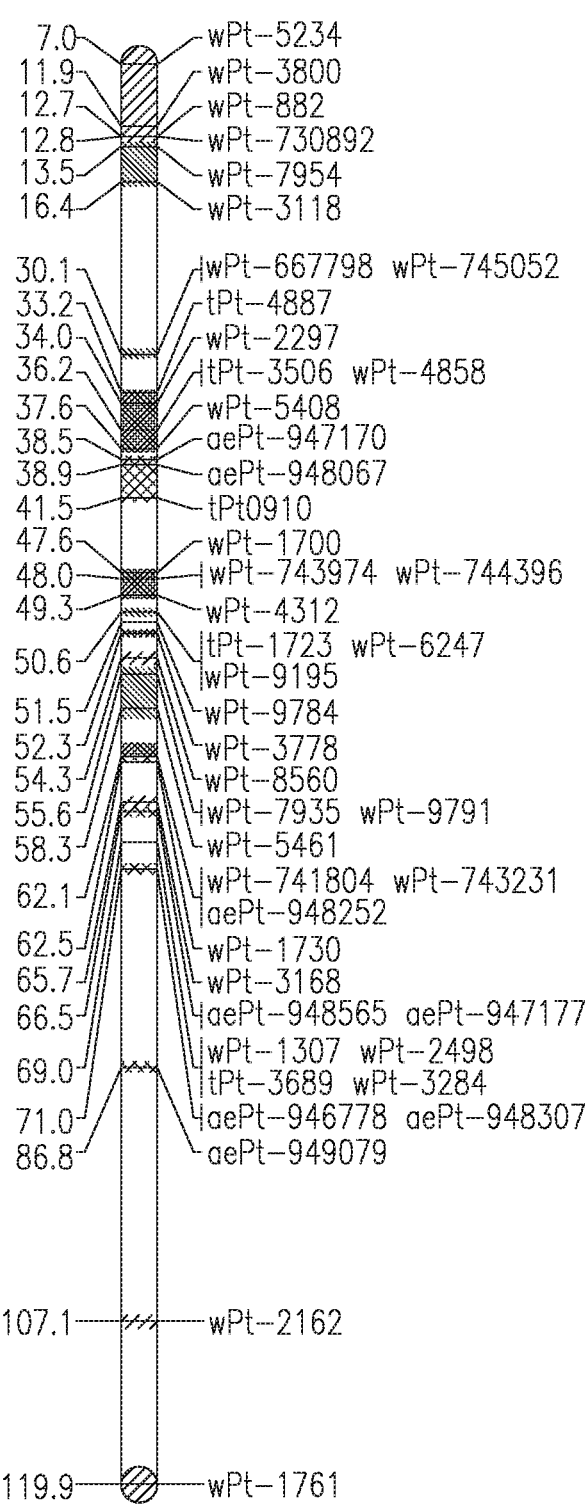
FIG 3 (cont. 2)

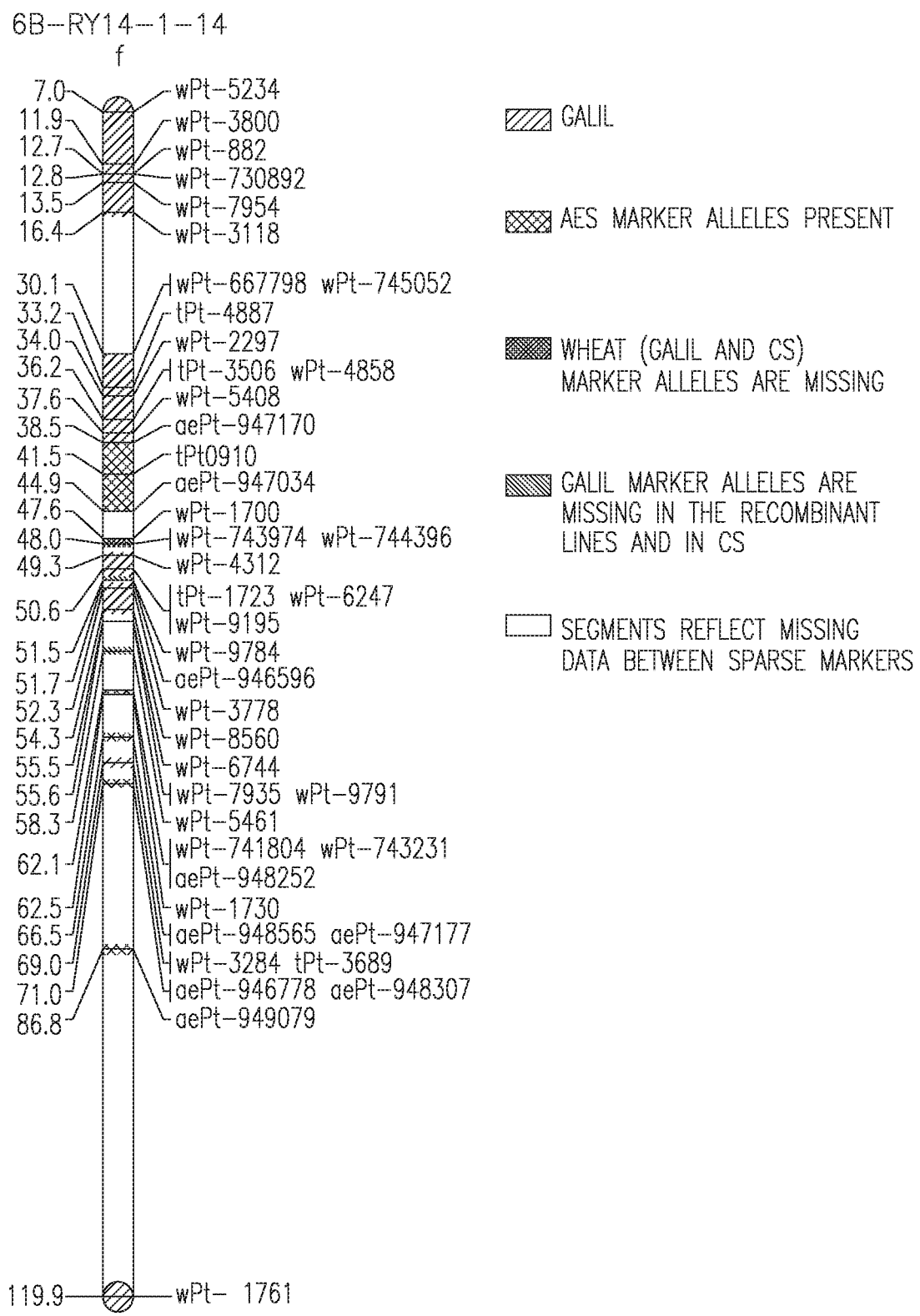
FIG 3 (cont. 3)

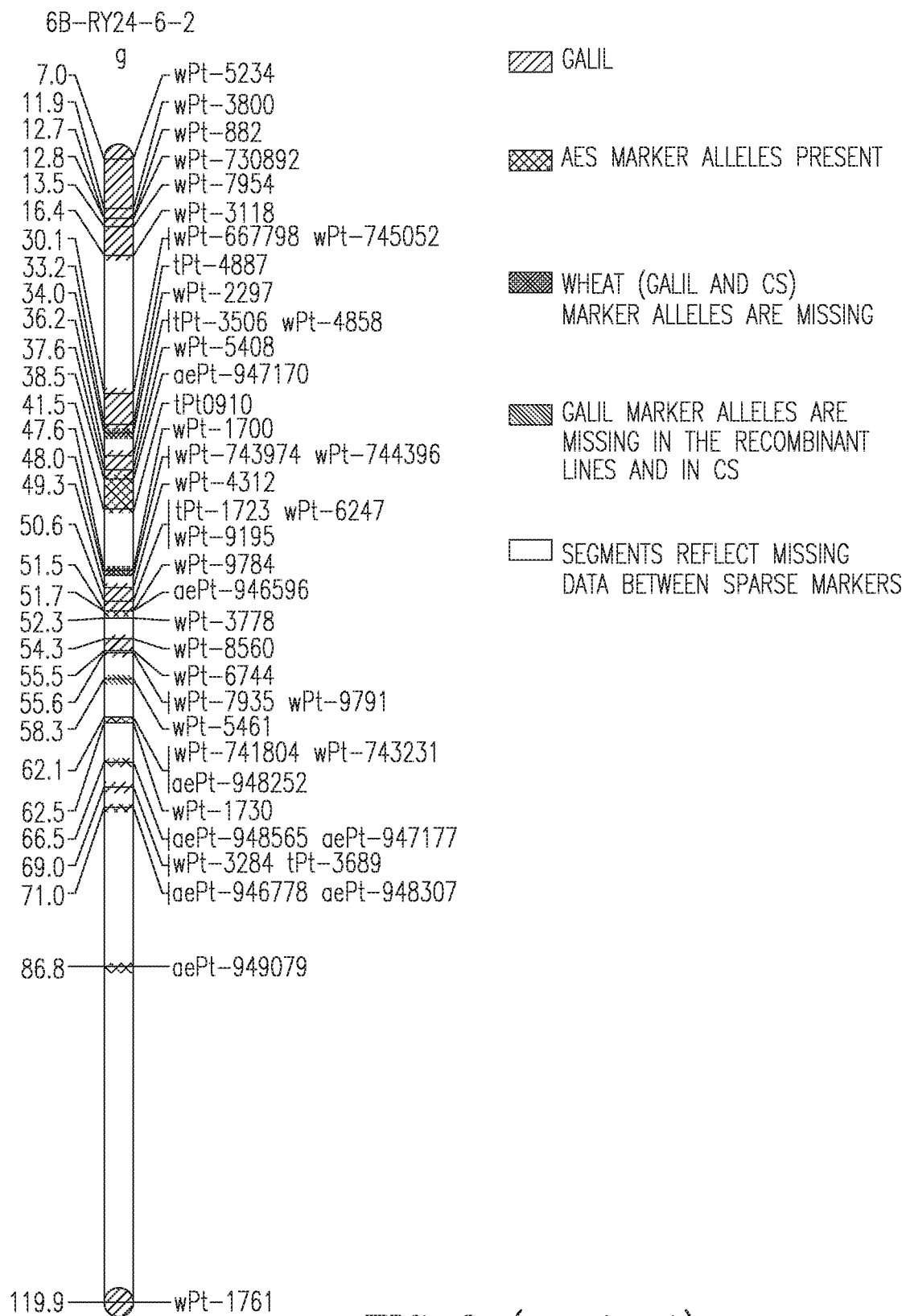
FIG 3 (cont. 4)

RESISTANCE TO RUST DISEASE IN WHEAT

The Sequence Listing in ASCII text file format of 2,480 bytes in size, created on Mar. 10, 2020, with the file name "2020-03-13SequenceListing_Millet2," filed in the U.S. Patent and Trademark Office on even date herewith, is hereby incorporated herein by reference.

FIELD OF THE INVENTION

The present invention relates to wheat plants that are resistant to leaf rust and/or stripe rust and to means and methods for producing same.

BACKGROUND OF THE INVENTION

Leaf rust, caused by the fungus *Puccinia triticina tritici* and stripe (yellow) rust, caused by *Puccinia striiformis tritici*, are major wheat diseases. Leaf rust and stripe rust cause tremendous yield losses annually. In the last years stripe rust outbreaks were reported in Australia, China, Pakistan, Central and West Asia, the Middle East (Syria and Turkey), India and U.S.A., indicating virulence changes of the pathogen (Wellings C R et al., 2012. CAB International, pp. 63-83). It was also shown that new stripe rust strains became adapted to higher inoculation temperatures that may account for the hazardous spread of the pathogen (Milus E A et al., 2006. Plant Disease, 90:847-852)

Sharon goatgrass (*Aegilops sharonensis* Eig) (AES) is a wild diploid (genome $S^{sh}S^{sh}$; 2n=14) relative of wheat. It is native to the coastal plain of Israel and south Lebanon, growing on stabilized dunes. Work done by Olivera et al. (Olivera P. D. et al. 2007. Plant Disease 91:942-950) on a representative sample of Sharon goatgrass lines collected in Israel and data from the Institute for Cereal Crops Improvement (ICCI, Israel) (Anikster Y. et al. 2005. Plant Disease 89:303-308) revealed that many accessions are highly resistant to inoculation with leaf rust or stripe rust pathogens. A recent evaluation of 1800 newly collected AES accessions at the ICCI confirmed the high frequency of resistance to these diseases in the species. Genetic analysis in a number of these lines (Olivera P. D. et al. 2008. Phytopathology 98:353-358) demonstrated monogenic inheritance of the resistance genes.

Although the Sharon goatgrass $S^{sh}$ genome is closely related to the B genome of tetraploid and hexaploid wheat, the two genomes cannot be regarded as being homologous. Gene transfer from Sharon goatgrass may therefore be more difficult as compared to transfer from donor species with homologous genomes. Technical problems (e.g. timing of flowering, time of anther dehiscence) and inherent low crossability with wheat result in very low hybrid seed set. Thereafter, pairing and chromosome segment exchange is rare.

Different procedures have been utilized to transfer genes from wild relatives to wheat (e.g. Feldman M. 1983. Acta Biol. Yugoslav. Genet. 15: 145-161; Millet E. 2007. Isr. J. Plant Sci. 55:277-287; Millet E et al., 2007. CAB International pp. 554-563; Qi L et al., 2007. Chrom. Res. 15:3-19; Kilian B et al., 2011. Aegilops. In Wild Crop Relatives: Genomic and Breeding Resources, Cereals. Edited by C. Kole Springer-Verlag, Berlin Heidelberg, pp. 1-76), many of which included production of an amphiploid by chromosome duplication of the interspecific hybrid and use of mutants of the Ph genes, which suppresses homoeologous pairing, and particularly the ph1b allele to allow such pairing.

In addition, Sharon goatgrass possesses gametocidal (Gc) genes (Maan S S. 1975. Crop Sci. 15:287-292; Endo T R. 1985. Jpn. J. Genet. 60: 125-135). Only few AES accessions have been used in genetic studies, but all of them showed a gametocidal effect as reflected in the failure to obtain the whole pure series of addition lines of AES. The finding that chromosome $4S^{sh}$ was always included in breeding progenies (Zhang H. et al 2001. Theor. Appl. Genet 103:518-525), supports the contention that Gc genes cause preferential transmission of their hosting chromosome. Their presence in a plant is accompanied by chromosome breakage of gametes not carrying the Gc genes, ultimately leading to semi-sterile spikes.

To avoid this gametocidal effect, an "anti-gametocidal" wheat mutant ($Gc2^{mut}$; Friebe B. et al. 2003. Chromosoma 111:509-517) that confers normal chromosome segregation rather than preferential transmission of the chromosome carrying the gametocidal gene may be used.

Despite its high resistance to different wheat diseases, Sharon goatgrass has hardly been exploited to improve wheat. Marais et al. (Marais G F et al., 2003. S Afr J Plant Soil 20:193-198) have identified potential useful resistance genes in Sharon goatgrass that were introgressed into common wheat chromosomes. In a further work leaf rust and stripe rust resistance genes, designated Lr56/Yr38, were transferred from Sharon goatgrass to chromosome 6A of common wheat (Marais G F et al. 2006. Euphytica 149:373-380). The translocation break occurred in the area of the long arm of wheat chromosome 6A. The Lr56/Yr38 translocation chromosome was found in effect to be most of the Sharon goatgrass chromosome with the terminal segment of its long arm replaced by a corresponding segment of wheat 6AL chromosome. In an attempt to reduce the amount of the transferred chromatin they employed recombination in the absence of the homoeologous pairing suppressor gene, Ph1, and obtained an intercalary sub-telomeric small introgression carrying the Lr56/Yr38 linked genes (Marais G F et al., 2010. Euphytica 171:15-22).

It is well accepted that using resistant varieties is the most efficient and economical way to control the leaf rust and stripe rust diseases. However, resistance conferred by many of the currently known genes has been overcome by the pathogenic fungi. In addition, the lines harboring the resistance genes are often inferior in their agricultural traits.

International (PCT) Patent Applications Publication Nos. WO 1995/029238 and WO 1999/045118 disclose genetic sequences which confer or otherwise facilitate disease resistance in plants such as against rust and mildew. The Application provides transgenic plants carrying the subject genetic sequences enabling the generation of disease resistant plants, particularly disease resistant crop varieties.

International (PCT) Patent Applications Publication No. WO 2013/082335 relates to new disease resistant crops and methods of creating new disease resistant crops. Particularly, the Application discloses a wheat genetic line comprising four highly effective disease resistance genes, Lr19, Sr25, Bdv3 and Qfhs.pur-7EL from the wheat-related grasses, *Thinopyrum intermedium* and *Th. Ponticum*, all on the long arm of wheat chromosome 7D. The genes are expected to remain in coupling in wheat genetic lines, resulting in wheat genetic lines with reduced susceptibility to yellow dwarf virus, *fusarium* head blight, stem rust, and leaf rust.

There is a recognized need for and it would be highly advantageous to have commercial agricultural wheat cultivars that are resistant to leaf and stripe rust.

SUMMARY OF THE INVENTION

The present invention provides wheat plants that are resistant to highly virulent forms of *Puccinia* fungi inducing leaf rust and/or stripe rust disease. Particularly, the present invention provides resistant wheat cultivars that are highly suitable for agricultural commercial use.

The present invention is based in part on the unexpected discovery that introgression of a minimal segment of an *Aegilops sharonensis* chromosome into the central region of wheat chromosome 6B confers high resistance to leaf rust and/or stripe rust disease, while not compromising the agronomic traits of the wheat germplasm, including when the introgression is into an elite wheat germplasm. Without wishing to be bound by any specific theory or a mechanism of action, this phenomenon may be attributed to the introgression of hitherto unknown loci of *Ae. sharonensis*, the loci harboring the genes conferring resistance to at least one of the pathogenic fungi *Puccinia triticina* and *Puccinia striiformis*.

Thus, according to one aspect, the present invention provides a wheat cultivar suitable for commercial growth comprising a genetic element comprising a segment of chromosome $6S^{sh}$ of *Aegilops sharonensis*, wherein the segment confers or enhances resistance of the wheat cultivar to a disease selected from the group consisting of leaf rust, stripe rust or a combination thereof.

According to some embodiments, the genetic element consists of the resistance-conferring or enhancing segment of *Ae. sharonensis* chromosome $6S^{sh}$.

According to certain exemplary embodiments, the resistance conferring segment is associated with at least one marker located on *Ae. sharonensis* chromosome $6S^{sh}$ between the short arm telomere (distance 0) and 120 cM. According to other exemplary embodiments, the at least one marker is located between the short arm telomere (distance 0) and 71 cM. According to some embodiments, the marker is located at a position selected from the group consisting of between position 0 and 16.4 cM and between 30 and 71 cM.

According yet additional embodiments, the segment of *Ae. sharonensis* chromosome $6S^{sh}$ confers resistance to leaf rust and the marker is selected from the group consisting of aePt947170 (mapped on 38.5 cM, having the nucleic acid sequence set forth in SEQ ID NO:1), aePt948067 (mapped on 38.9 cM), Pt0910 (mapped on 41.5 cM) and any combination thereof. According to further embodiments, the *Ae. sharonensis* chromosome $6S^{sh}$ segment confers resistance to stripe rust and the marker is selected from the group consisting of aePt947170 (mapped on 38.5 cM, having the nucleic acid sequence set forth in SEQ ID NO:1), tPt0910 (41.5 cM, having the nucleic acid sequence set forth in SEQ ID NO:2), aePt948252 (62.1 cM), aePt948565 and aePt947177 (66.5 cM), aePt949079 (86.8 cM) and any combination thereof.

According to additional embodiments, the segment of *Ae. sharonensis* chromosome $6S^{sh}$ confers resistance to leaf rust and stripe rust and the marker is selected from the group consisting of aePt947170 (mapped on 38.5 cM, having the nucleic acid sequence set forth in SEQ ID NO:1), tPt0910 (41.5 cM, having the nucleic acid sequence set forth in SEQ ID NO:2) and a combination thereof.

According to certain embodiments, the genetic element comprising the *Ae. sharonensis* chromosome segment is incorporated within chromosome 6B of the wheat cultivar. According to further embodiments, the *Ae. sharonensis* chromosome segment is located in the central part of the wheat cultivar chromosome 6B.

According to certain exemplary embodiments, the *Ae. sharonensis* chromosome segment confers or enhances resistance to leaf rust and to stripe rust.

The wheat plant of the present invention is a cultivar suitable for commercial growth, but it is not restricted to a specific species, strain or variety. According to certain exemplary embodiments, the wheat cultivar comprising the genetic element derived from *Ae. sharonensis* chromosome is of a species selected from the group consisting of *Triticum turgidum* and *Triticum aestivum*.

According to certain embodiments, the wheat plant is an inbred plant homozygous for chromosome 6B comprising the *Ae. sharonensis* chromosome segment. According to other embodiments, the wheat plant is a hybrid heterozygous plant comprising a native wheat chromosome 6B and chromosome 6B comprising the *Ae. sharonensis* chromosome segment.

According to certain embodiments, the wheat cultivar comprising the *Ae. sharonensis* chromosome $6S^{sh}$ segment is resistant to a disease selected from the group consisting of leaf rust, stripe rust or a combination thereof. According to certain exemplary embodiments, the wheat cultivar is resistant to leaf rust and to stripe rust.

According to some embodiments, the wheat cultivar comprises the functional homoeologous pairing suppressor gene Ph1. It is to be explicitly understood that the wheat is devoid of the ph1 mutant allele(s).

According to additional embodiments, the wheat cultivar is devoid of *Ae. sharonensis* gametocidal Gc2 gene and/or a mutant thereof.

According to certain embodiments, the rust disease is caused by a species of the fungus *Puccinia*. According to certain exemplary embodiments, leaf rust is caused by *Puccinia triticina*. According to certain typical embodiments, the leaf rust is caused by *Puccinia triticina tritici*. According to other exemplary embodiments, stripe rust is caused by *Puccinia striiformis*. According to certain typical embodiments, the stripe rust is caused by *Puccinia striiformis tritici*.

According to certain embodiments, the wheat plant cultivar comprising the genetic element comprising *Ae. sharonensis* chromosome segment has equivalent agronomical traits compared to a corresponding cultivar lacking the introduced chromosome segment. According to certain embodiments, the agronomical traits are selected from, but not limited to, growth rate, yield, resistance to abiotic stresses and resistance to pathogens other than the *Puccinia*. According to certain exemplary embodiments, the wheat cultivar is an elite cultivar.

It is to be explicitly understood that the wheat cultivars of the present invention are fertile. Seeds and any other plant part that can be used for propagation, including isolated cells and tissue cultures are also encompassed within the scope of the present invention. It is to be understood that the plant produced from said seeds or other propagating material comprises the *Ae. sharonensis* $6S^{sh}$ chromosome segment that confers or enhances resistance to a disease selected from the group consisting of leaf rust, stripe rust or a combination thereof.

The present invention discloses a hitherto unknown specific segment of *Ae. sharonensis* $6S^{sh}$ chromosome that is associated with resistance to leaf rust and/or stripe rust disease caused by the fungus *Puccinia*. The leaf rust-resistance conferring segment is associated with an *Ae. sharonensis* DNA marker selected from the group consisting of aePt947170 (mapped on 38.5 cM, having the nucleic acid sequence set forth in SEQ ID NO:1), aePt948067 (38.9 cM), Pt0910 (41.5 cM, having the nucleic acid sequence set forth in SEQ ID NO:2) and any combination thereof. The stripe rust-resistance conferring segment is associated with an *Ae.* sharonensis DNA marker selected from the group consisting of aePt947170 (mapped on 38.5 cM, having the nucleic acid sequence set forth in SEQ ID NO:1), tPt0910 (41.5 cM, having the nucleic acid sequence set forth in SEQ ID NO:2) aePt948252 (62.1 cM), aePt948565 and aePt947177 (66.5 cM), aePt949079 (86.8 cM) and any combination thereof.

According to another aspect, the present invention provides an isolated polynucleotide comprising a nucleic acid sequence conferring resistance to at least one of leaf rust disease, stripe rust disease or a combination thereof, wherein the nucleic acid sequence is derived from a segment of $Ae.$ $sharonensis$ chromosome $6S^{sh}$.

According to some embodiments, the polynucleotide comprises a nucleic acid sequence conferring resistance to the leaf rust disease. According to these embodiments, the polynucleotide comprises the sequence of at least one marker selected from the group consisting of aePt947170 (SEQ ID NO:1), aePt948067 and tPt0910 (SEQ ID NO:2).

According to other embodiments, the polynucleotide comprises a nucleic acid sequence conferring resistance to the stripe rust disease. According to these embodiments, the polynucleotide comprises the sequence of at least one marker selected from the group consisting of aePt947170 (SEQ ID NO:1), tPt0910 (SEQ ID NO:2), aePt948252, aePt948565, aePt947177 and aePt949079.

According to additional embodiments, the polynucleotide comprises a nucleic acid sequence conferring resistance to the leaf rust disease and the stripe rust disease. According to these embodiments, the polynucleotide comprises the sequence of the markers aePt947170 (SEQ ID NO:1) and tPt0910 (SEQ ID NO:2).

According to yet additional aspect the present invention provides a method for producing a wheat cultivar resistant to at least one rust disease, the method comprises introducing into a wheat cultivar susceptible to the disease a genetic element comprising a segment of chromosome $6S^{sh}$ of $Aegilops\ sharonensis$, wherein the segment comprises at least one locus conferring resistance to at least one of leaf rust disease, stripe rust disease or a combination thereof, thereby producing a wheat cultivar resistant to said at least one rust disease.

According to certain embodiments, the wheat cultivar is suitable for commercial growth.

According to some embodiments, the genetic element consists of the resistance-conferring segment of $Ae.$ $sharonensis$.

According to certain exemplary embodiments, the resistance conferring segment is associated with at least one marker located on $Ae.$ $sharonensis$ chromosome $6S^{sh}$ between the short arm telomere (distance 0) and 120 cM. According to other exemplary embodiments, the at least one marker is located between the short arm telomere (distance 0) and 71 cM. According to some embodiments, the marker is located at a position selected from the group consisting of between position 0 and 16.4 cM and between 30 and 71 cM.

According to additional embodiments, the genetic element comprises an $Ae.$ $sharonensis$ DNA marker selected from the group consisting of aePt947170 (mapped on 38.5 cM, having the nucleic acid sequence set forth in SEQ ID NO:1), tPt0910 (41.5 cM, having the nucleic acid sequence set forth in SEQ ID NO:2) and a combination thereof.

According to yet additional embodiments, the genetic element confers resistance to leaf rust and the DNA marker is selected from the group consisting of aePt947170 (mapped on 38.5 cM, having the nucleic acid sequence set forth in SEQ ID NO:1), aePt948067 (38.9 cM), Pt0910 (41.5 cM, having the nucleic acid sequence set forth in SEQ ID NO:2) and any combination thereof. According to further embodiments, the genetic element confers resistance to stripe rust-resistance and the DNA marker is selected from the group consisting of aePt947170 (mapped on 38.5 cM, having the nucleic acid sequence set forth in SEQ ID NO:1), tPt0910 (41.5 cM, having the nucleic acid sequence set forth in SEQ ID NO:2) aePt948252 (62.1 cM), aePt948565 and aePt947177 (66.5 cM), aePt949079 (86.8 cM) and any combination thereof.

According to certain embodiments, the genetic element is introduced into chromosome 6B of the susceptible wheat cultivar. According to certain exemplary embodiments, the genetic element is introduced into the central part of the wheat chromosome 6B.

Any method as is known to a person skilled in the art can be used to introduce the $Ae.$ $sharonensis$ chromosome $6S^{sh}$ segment or a resistance-conferring part thereof or a resistance-conferring polynucleotide into a susceptible wheat cultivar.

According to certain exemplary embodiments, the genetic element is introduced by introgression.

According to certain embodiments, the rust disease is selected from the group consisting of leaf rust disease and stripe rust disease caused by the fungi $Puccinia\ triticina$ and $Puccinia\ striiformis$ respectively. According to certain exemplary embodiments, the leaf rust disease is caused by $Puccinia\ triticina\ tritici$. According to other exemplary embodiments, the stripe rust disease is caused by $Puccinia\ striiformis\ tritici$.

According to certain embodiments, selecting plants resistant to the rust disease is performed by inoculating the plants with the respective fungus and selecting phenotypically resistant plants. According to certain exemplary embodiments, the inoculation and selection is performed at the seedling stage of the plants.

According to other embodiment, selecting plants resistant to the rust disease is performed by detecting the presence of the $Ae.$ $sharonensis$ resistance conferring segment of chromosome $6S^{sh}$ described herein within the genome of the wheat plant. Any method as is known in the art can be used to detect the chromosome segment. According to certain exemplary embodiments, detection is performed by identifying the markers located on the chromosome segment as described herein.

According to certain embodiments, the plants are further selected to be devoid of the ph1 mutant gene.

According to certain additional aspects, the present invention provides a wheat cultivar suitable for commercial growth comprising a genetic element comprising a segment of chromosome $6S^{sh}$ of $Aegilops\ sharonensis$, wherein the segment confers or enhances resistance of the wheat cultivar to a disease caused by the fungus $Puccinia$.

According to additional aspects, the present invention provides a method for producing a wheat cultivar resistant to at least one disease caused by the fungus $Puccinia$, the method comprises introducing into a wheat cultivar susceptible to the disease a genetic element comprising a segment of chromosome 6S' of $Aegilops\ sharonensis$, wherein the segment comprises at least one locus conferring resistance to the at least one fungal disease, thereby producing a wheat cultivar resistant to said at least one fungal disease.

Other objects, features and advantages of the present invention will become clear from the following description and drawings.

DETAILED DESCRIPTION OF THE INVENTION

Figure 1:
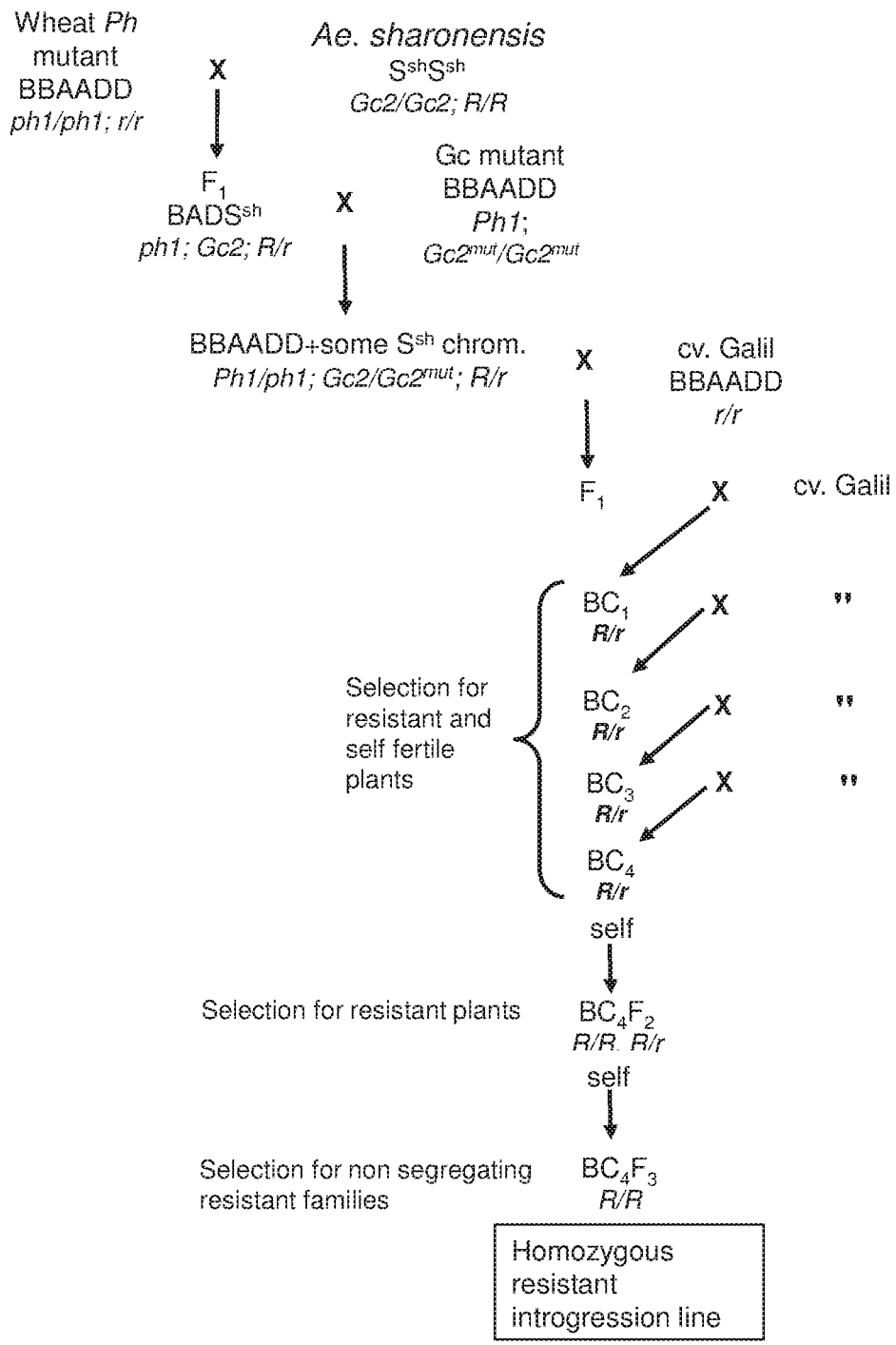
FIG. 1 presents the procedure for the transfer of a disease resistance gene (R) from $Ae.$ $sharonensis$ to wheat using haploid hybrid with homoeologous pairing mutation (ph1). Gametocidal effect of Gc2 of *Ae. sharonensis* is overcome by "anti-gametocidal" mutant (Ga2$^{mut}$).

The present invention provides wheat plants resistant to various species and phytotypes of the fungus *Puccinia*, including highly virulent types, which cause rust diseases responsible for significant losses of wheat crops. The present invention now provides wheat cultivars that are not only resistant to the deleterious fungus but also keep the original elite agronomic traits of the wheat. The improved lines result in increased profitability for wheat and in a reduction of fungicide use, which by itself is a significant component of sustainable agriculture. The introgression lines of the invention can be incorporated in spring or winter wheat breeding program for leaf rust and/or yellow rust resistance in the U.S.A. and Israel as well as worldwide. The present invention further provides means to track the resistance gene in breeding programs.

Definitions

The term "plant" is used herein in its broadest sense. It also refers to a plurality of plant cells that are largely differentiated into a structure that is present at any stage of a plant's development. Such structures include, but are not limited to, a root, stem, shoot, leaf, flower, petal, fruit, etc. According to certain exemplary embodiments, the term "wheat plant" refers to *Triticum turgidum* subsp. durum (tetraploid wheat=macaroni wheat) and *T. aestivum* subsp. *aestivum* (hexaploid wheat=bread wheat=common wheat) of the tribe Triticeae, family Poaceae (Gramineae).

The term "line" as is used herein refers to a plant that is homozygous and true-breeding by self pollination but not necessarily used as a variety. According to certain embodiments, the line is a wheat line.

The term "cultivar" is used herein to denote a plant having a biological status other than a "wild" status, which "wild" status indicates the original non-cultivated or natural state of a plant or accession. The term "cultivar" (for cultivated plants) includes, but is not limited to, semi-natural, semi-wild, weedy, traditional cultivar, landrace, breeding material, research material, breeder's line, synthetic population, hybrid, founder stock/base population, inbred line (parent of hybrid cultivar), segregating population, mutant/genetic stock, and advanced/improved cultivar. The term as used herein includes registered as well as non-registered lines. Examples of cultivars include such cultivated varieties that belong to the species *Triticum turgidum* and *Triticum aestivum*, including, but not limited to, "Chinese Spring" (CS) and "Galil".

The terms "*Aegilops sharonensis*" or "*Ae. sharonensis*" or "AES" are used herein interchangeably and relate to a wild type plant resistant to a disease caused by a fungus of the species *Puccinia*, particularly by *Puccinia triticina* and/or *Puccinia striiformis*. According to certain exemplary embodiments, the term refers to *Ae. sharonensis* accession TH548 that is resistant to both *Puccinia triticina* and *Puccinia striiformis* and is thus resistant to the leaf rust and stripe rust diseases. Seeds of *Ae. sharonensis* accession TH548 have been deposited with NCIMB Ltd., Ferguson Building, Craibstone Estate, Bucksburn, Aberdeen, AB21 9YA Scotland on Jan. 31, 2020 and received deposit accession number NCIMB 43567.

The terms "resistant" and "resistance" encompass both partial and full resistance to infection. A rust-resistant AES plant may either be fully resistant or have low levels of susceptibility to infection by the fungus *Puccinia*, particularly by *Puccinia triticina*, and/or *Puccinia striiformis*, more particularly by *Puccinia triticina tritici* and/or *Puccinia striiformis tritici*. A rust-susceptible wheat plant may be either non-resistant or have low levels of resistance to these fungi.

The term "locus" (plural "loci") is defined herein as the position that a given gene occupies on a chromosome of a given species.

The term "heterozygous" as is used herein means a genetic condition existing when different alleles reside at corresponding loci on homologous chromosomes.

The term "homozygous" as is used herein, means a genetic condition existing when identical alleles reside at corresponding loci on homologous chromosomes.

As used herein, the term "hybrid" refers to any offspring of a cross between two genetically unlike individuals, including but not limited to the cross between two inbred lines.

As used herein, the term "inbred" means a substantially homozygous individual or line.

The terms "introgression" "introgressed" and "introgressing" refer to the transmission of a desired allele(s) of a gene or trait locus from a genetic background of one species, variety or cultivar into the genome of another species, variety or cultivar. In one method, the desired allele(s) can be introgressed through a sexual cross between two parents, wherein one of the parents has the desired allele in its genome. The desired allele can include desired gene or genes, a marker locus, a QTL or the like.

The terms "genetic engineering", "transformation" and "genetic modification" are all used herein for the transfer of isolated and cloned genes into the DNA, usually the chromosomal DNA or genome, of another organism, or to the modification of a gene within the plant genome.

As used herein, the term "plant part" typically refers to a part of the wheat plant, including single cells and cell tissues such as plant cells that are intact in plants, cell clumps and tissue cultures from which wheat plants can be regenerated. Examples of plant parts include, but are not limited to, single cells and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, calli, and the like.

As used herein, the term "population" refers to a genetically heterogeneous collection of plants sharing a common genetic derivation.

The term "linkage group" as used herein refers to all of the genes or genetic traits that are located on the same chromosome. Within the linkage group, those loci that are close enough together will exhibit linkage in genetic crosses. Since the probability of crossover increases with the physical distance between genes on a chromosome, genes whose locations are far removed from each other within a linkage group may not exhibit any detectable linkage in direct genetic tests.

The terms "molecular marker" or "DNA marker" are used herein interchangeably and refer to a molecular indicator that is used in methods for visualizing differences in characteristics of nucleic acid sequences. Examples of such indicators are diversity array technology (DArT) markers, restriction fragment length polymorphism (RFLP) markers, amplified fragment length polymorphism (AFLP) markers, single nucleotide polymorphisms (SNPs), insertion mutations, microsatellite markers, sequence-characterized amplified regions (SCARs), cleaved amplified polymorphic sequence (CAPS) markers or isozyme markers or combinations of the markers described herein which defines a specific genetic and chromosomal location.

Stripe rust (also designated yellow rust, caused by the fungus *Puccinia striiformis*) and leaf rust (caused by *Puccinia triticina*) are two devastating wheat diseases causing enormous annual yield losses. The fungal pathogens are changing frequently, giving rise to new virulent types and thus overcoming the currently deployed resistance genes. Consequently, the primary wheat gene pool is becoming exhausted and new resistance genes are required. Wild relatives of wheat are yet an untapped resistance gene pool.

According to one aspect, the present invention provides a wheat plant cultivar comprising a genetic element comprising a segment of chromosome 6S" of *Aegilops sharonensis*, wherein the segment confers, enhances, or otherwise facilitates resistance of the wheat plant cultivar to a disease selected from the group consisting of leaf rust, stripe rust or a combination thereof.

The present invention discloses a novel segment of *Ae. sharonensis* chromosome 6S' that carries the resistance locus or loci.

The segment was found by producing wheat introgression lines comprising a chromosome segment of *Ae. sharonensis*. Unexpectedly, using a wheat line carrying the ph1b mutant gene, a few seeds were obtained. The Ph1 locus restricts chromosome pairing and recombination at meiosis to true homologues. Therefore, a mutated wheat plant comprising a non active Ph1 gene (i.e. a plant homozygous for the ph1b mutation) was used. This approach allowed rapid gene introgressions due to the reduced number of backcross generations required to obtain resistant plants having the characteristics of the elite wheat cultivar used as a backcross recurrent parent.

*Ae. sharonensis* comprises gametocidal genes, a group of selfish genes that induce chromosome breakage in gametes not having them, thus preventing the transmission of these gametes. This mechanism ensures that only gametes containing the gametocidal gene are transmitted. Gametocidal (Gc) genes were detected on chromosome 4S" of certain lines of *Ae. sharonensis* (Maan, 1975, ibid; Endo, 1985, ibid). An "anti-gametocidal" mutant wheat line that suppresses the action of *Ae. sharonensis* Gc2 gene was generated by Friebe et al., 2003, ibid). This line has a translocated 4BL.4BS-4$S^{sh}$S chromosome (4B with a terminal 4$S^{sh}$S segment) carrying a Gc2 gene that was mutated by EMS and is designated Gc2$^{mut}$. Normal transmission of mutant and wild type alleles was observed in heterozygotes Gc2/Gc2$^{mut}$ rather than preferential transmission of the Gc2. This mutant allows exclusion of the undesired 4$S^{sh}$ chromosome in wheat lines having introgression from *Ae. sharonensis*

Figure 4:
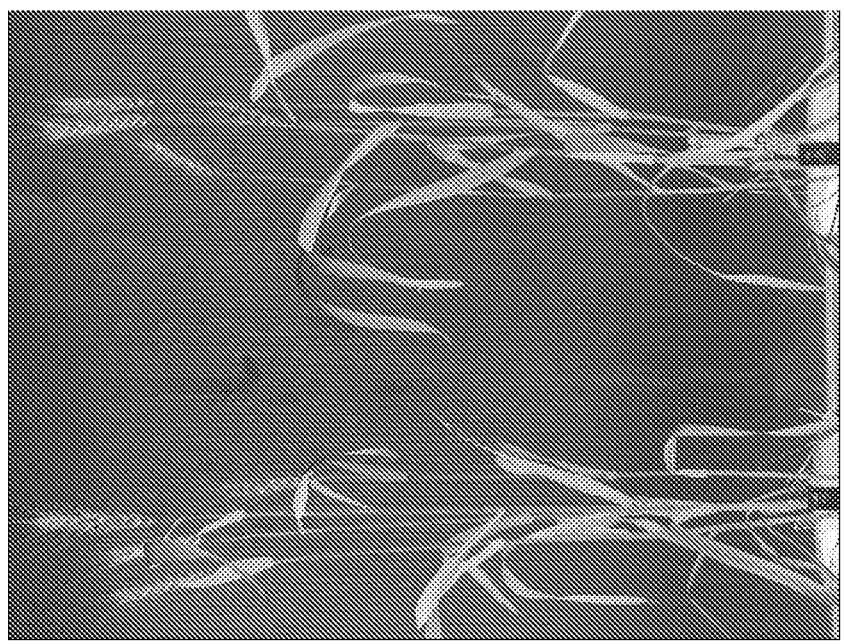
FIG. 4 shows the phenotypes of the wheat cultivar Galil and of a selected BC$_4$F$_4$ introgressed line comprising the *Ae. sharonensis* yellow rust resistance segment.

In the early backcross generations offspring with low seed set and offspring with complete seed set were obtained. Plants with 40%-60% non-fertile spikes carry the Gc2 gene. This phenomenon was used to remove the Gc2 gene by selecting only fully fertile offspring. Thus the procedure of the present invention yielded fertile resistant backcross progenies that phenotypically resembled their recurrent parental cultivar Galil, an elite cultivar highly suitable for commercial growth (FIG. 1 and FIG. 4).

Due to the repeated backcrosses with the recurrent elite cultivar, the resistant $BC_4$ progenies were devoid of the mutant ph1b gene, carrying a functional Ph1 gene.

Hitherto, attempts to introgress chromosome segments of donor AES into wheat resulted in significant genetic drag of undesirable traits from the donor into the wheat. Also, the chromatin exchange between the donor AES and wheat resulted in removal of essential wheat chromatin and obtaining an inferior wheat plant.

Figure 2:
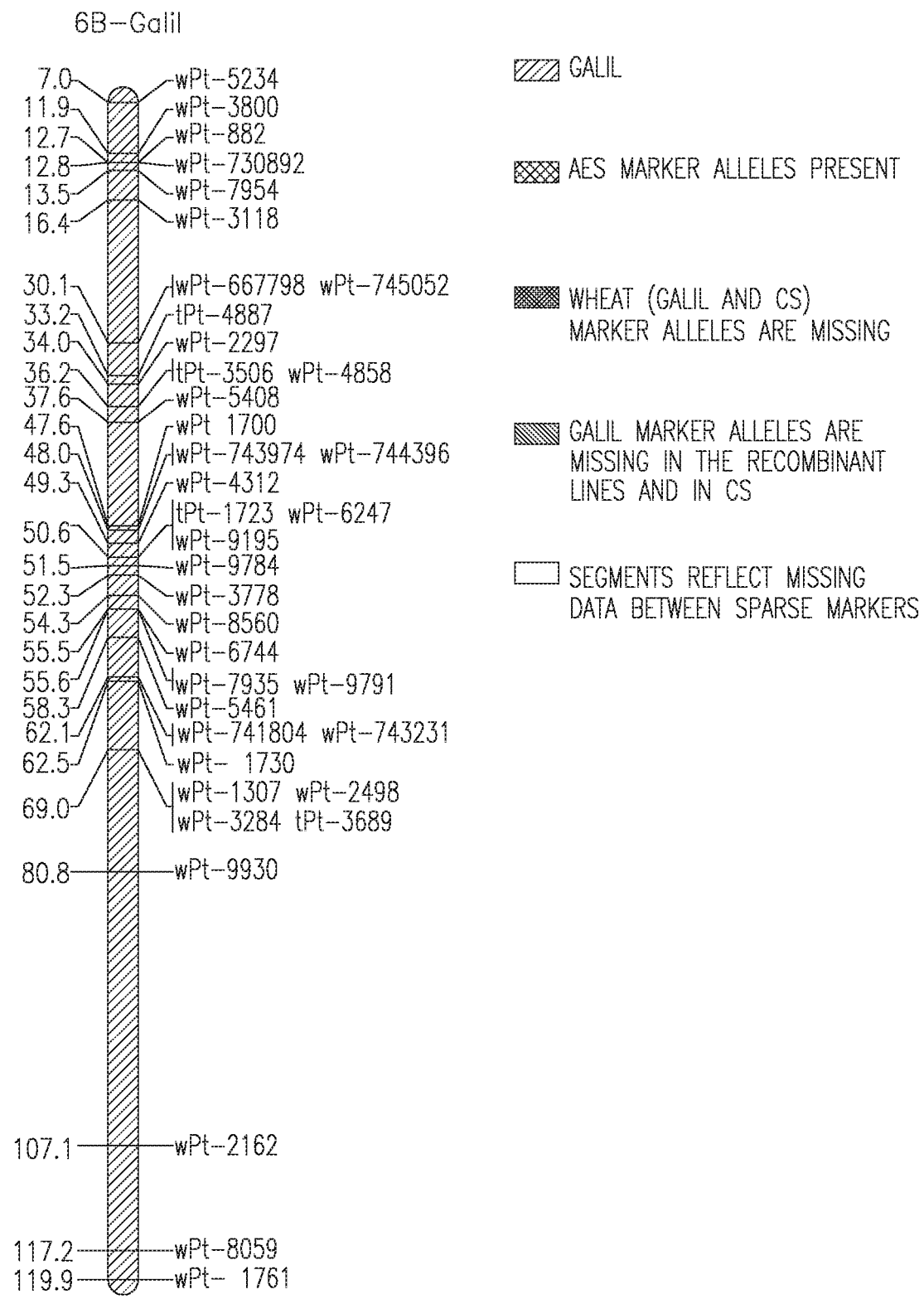
FIG. 2 shows DArT marker map of cv. Galil and its derived leaf rust resistant recombinant lines. Linkage groups are identified by different patterns. Chromotypes are denoted by small letters (a-c).
Figure 3:
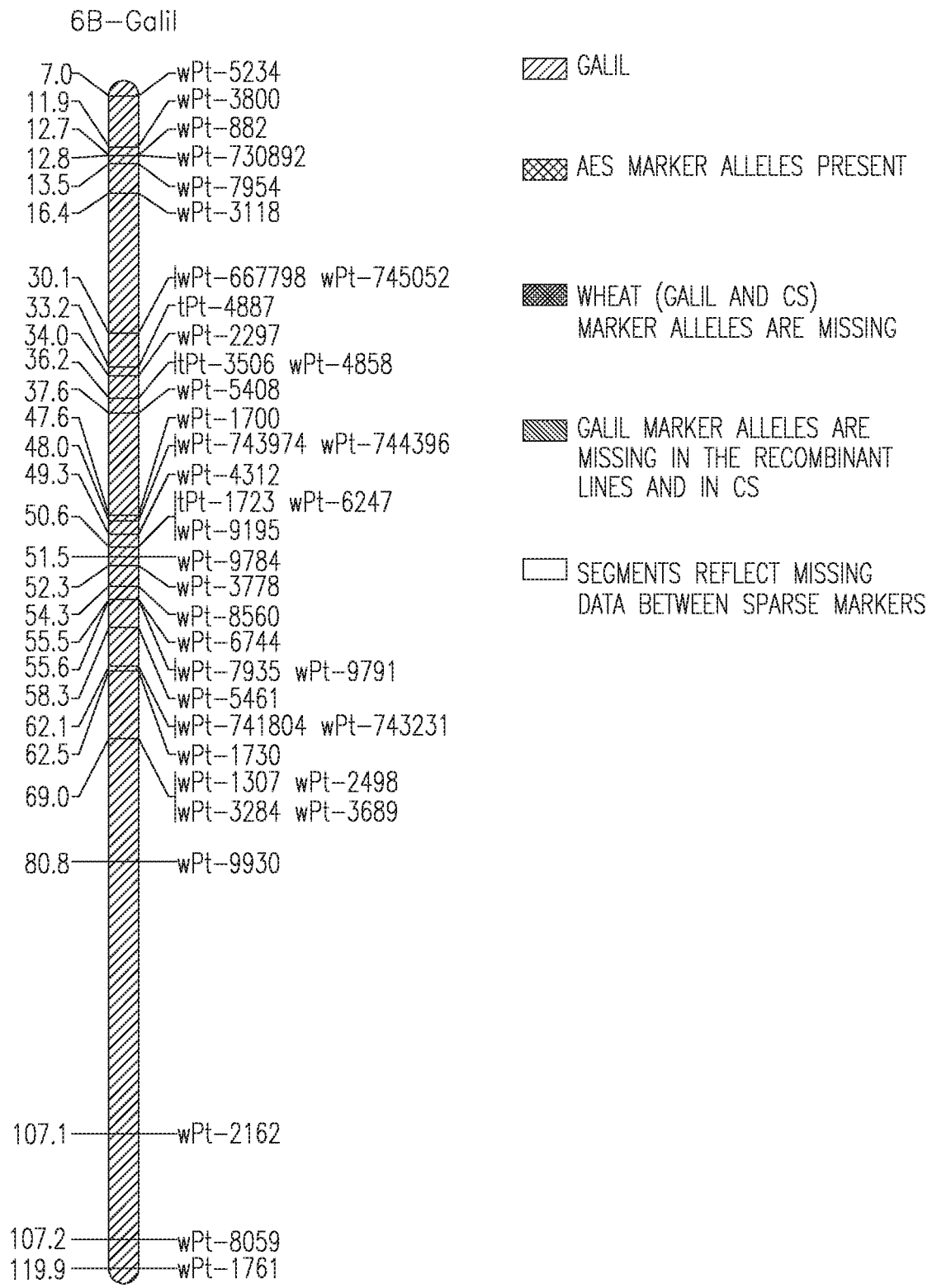
FIG. 3 shows DArT marker map of cv. Galil and its derived stripe rust resistant recombinant lines. Linkage groups are identified by different patterns Chromotypes are denoted by small letters (d-g).
Figure 5:
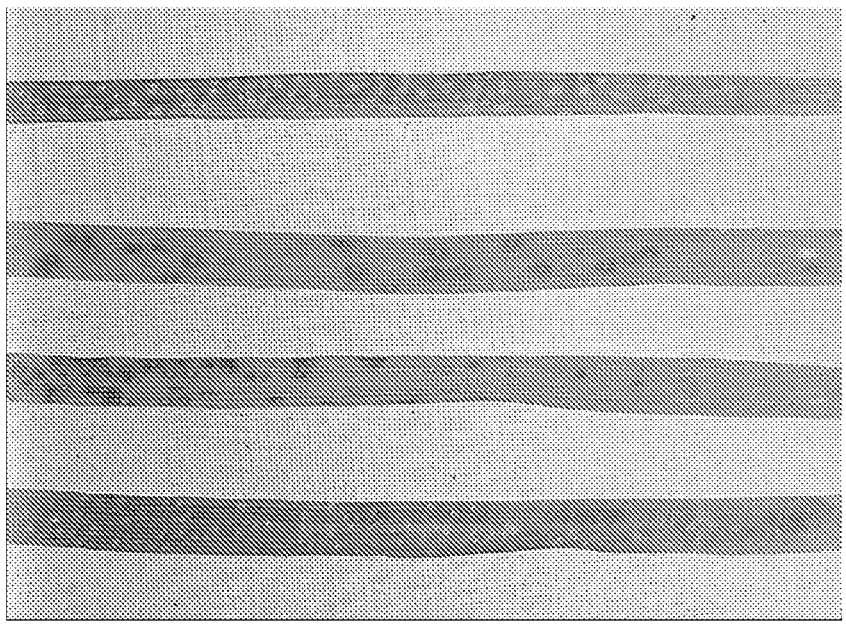
FIG. 5 shows the reactions of leaves taken from wheat cultivar Galil, ph1b mutant of CS wheat (mTA03) and two leaves taken from introgressed line comprising the *Ae. sharonensis* yellow rust resistance segment to inoculation with leaf rust pathogen.

With the availability of an AES maps (Olivera P D et al., 2013. Genome, 56:367-376; Moscou M.—unpublished data), DArT mapping is a time and cost effective procedure to assess introgressions. Yet, most of the polymorphic AES DArT markers have not been mapped. Considering the homoeology between wheat 6B and AES 6$S^{sh}$ chromosomes, in many instances the information of absent wheat (cv. Galil) DArT marker alleles in a tested line were used as an indication for substitution by AES chromatin. FIG. 2 and FIG. 3 show the construction of the recombinant chromosome including AES chromosome 6$S^{sh}$ segments within wheat Chromosome 6B. The polymorphic AES markers used in the study presented herein were mapped using segregating AES populations, while the wheat DArT markers map was prepared from a segregating population of wheat. Despite the expected synteny between genes of these two closely related species, estimates of the distance between genes within AES and wheat may be species dependent. Hence, the construction of any of the recombinant chromosomes using both AES and wheat DArT markers as they appear in FIGS. 2 and 3 may not reflect the exact chromotype composition.

Almost all of the polymorphic wheat markers associated with the target introgression events in the various lines belonged to chromosome 6B, and the AES informative markers belonged to 6$S^{sh}$ chromosome. These mapping results show that wheat chromatin of chromosome 6B was replaced by homoeologous AES chromatin. All of the resistant lines carried 6$S^{sh}$ segments of various lengths and few chromatin substitutions were common to all lines tested.

Resistant plants from the backcross offspring families were phenotyped against certain North American races of the fungus *Puccinia* causing leaf rust and yellow rust diseases.

From correspondence between resistant genotypes and mapping data of the 6B-6$S^{sh}$ recombinants, it was concluded that the translocated AES 6$S^{sh}$ segment(s) carry gene(s) for leaf rust and/or stripe rust resistance.

The possibility that the wheat "anti-gametocidal" (AG) mutant line used in the course of production of the resistant wheat plant of the present invention is responsible for the acquired resistance due to its AES translocation was ruled out; this mutant was found to be susceptible (IT=3 in a scale of 4) both to leaf rust isolate #526-24 and to stripe rust isolate #5006. Apparently, the alien translocation from 4S$^{sh}$L (Friebe et al. 2003) does not carry resistance genes against these isolates.

According to certain exemplary embodiments, the resistance conferring segment is associated with at least one DNA marker located on *Ae. sharonensis* chromosome 6S$^{sh}$ between the short arm telomere (distance 0) and 120 cM. According to other exemplary embodiments, at least one DNA marker is located between the short arm telomere (distance 0) and 71 cM. According to some embodiments, the DNA marker is located at a position selected from the group consisting of between position 0 and 16.4 cM and between 30 and 71.

According to additional embodiments, the genetic element comprises an *Ae. sharonensis* DNA marker selected from the group consisting of aePt947170 (mapped on 38.5 cM and having the nucleic acid sequence set forth IN SEQ ID NO:1), tPt0910 (mapped on 41.5 cM and having the nucleic acid sequence set forth IN SEQ ID NO:2) and a combination thereof.

According yet additional embodiments, the genetic element confers resistance to leaf rust and the DNA marker is selected from the group consisting of aePt947170 (mapped on 38.5 cM, having the nucleic acid sequence set forth IN SEQ ID NO:1), aePt948067 (mapped on 38.9 cM), Pt0910 (mapped on 41.5 cM, having the nucleic acid sequence set forth IN SEQ ID NO:2) and any combination thereof. According to further embodiments, the genetic element confers resistance to stripe rust disease and the DNA marker is selected from the group consisting of aePt947170 (mapped on 38.5 cM, having the nucleic acid sequence set forth IN SEQ ID NO:1), tPt0910 (mapped on 41.5 cM, having the nucleic acid sequence set forth IN SEQ ID NO:2) aePt948252 (mapped on 62.1 cM), aePt948565 and aePt947177 (mapped on 66.5 cM), aePt949079 (mapped on 86.8 cM) and any combination thereof.

In some of the recombinant lines, long translocated segments, at least in genetic terms, may carry undesirable alien alleles (genetic drag), which may reduce grain yield and quality. Therefore, the length of the alien segment carrying the resistance gene is significantly reduced, based on fine mapping and annotation of candidate genes.

Methods for fine mapping and identification of candidate genes are well known to one skilled in the art. According to some embodiments, fine mapping is performed by saturating the region carrying the resistance gene with markers followed by the use of comparative genomics and RNA profiling data to identify candidate genes.

In some exemplary embodiments, mapping the region containing the resistance gene is based on two sequencing approaches. Both approaches use the basic idea of bulk segregation analysis coupled with next generation sequencing. DNA is isolated from homozygous resistant plants and from susceptible $F_2$ plants, and two bulks are created, one containing the resistance allele and one containing the susceptible allele. In the first approach, the basic idea of the SHOREmapping (Schneeberger K. et al., 2009. Nature Methods 6:550-551) and whole genome shotgun (WGS) sequence is followed. In the second approach, before the sequencing is conducted, the complexity of the genome is reduced, for example by using the Roche-Nimblegen whole exome in-solution hybridization-based sequence capture platform targeting 61.6 Mb of sequence in the barley genome (Mascher M. et al., 2013. The Plant Journal DOI: 10.1111/tpj.12294). The barley exome capture platform has been shown to work reasonably well on hexaploid wheat, with approximately 50% of the reads map to the barley genome (Mascher et al., 2013, ibid), and is thus expected to work at approximately the same efficiency in *Ae. sharonensis*. In both sequencing datasets (WGS and exome capture), the reads are aligned to the barley genome sequence (The International Barley Genome Sequencing Consortium, 2012. Nature 491:711-716). Sequence reads that exhibit allelic bias are reads that map close to the gene. A comparative genomics with the barley, wheat, *Aegilops tauschii*, Brachypodium and rice genomes are then conducted to help determining the order of the markers that are linked to the gene and to identify candidate genes. Candidate genes are further identified by examining the gene expression patterns in the RNA-seq dataset described below. Those genes that are not expressed during infection are not candidates as being the resistance gene. SNPs found in the sequencing data are used for additional fine mapping.

Introducing a genetic element comprising the AES chromosome $6S^{sh}$ segment conferring resistance to leaf rust, stripe rust or to the combination thereof, and producing plant resistant to at least one of these diseases can be performed by any method as is known to a person skilled in the art. It is to be explicitly understood that in the resistant wheat cultivar produced, the segment of *Ae sharonensis* chromosome $6S^{sh}$ is not in its natural background.

A nucleic acid (preferably DNA) sequence comprising the AES chromosome segment conferring resistance as disclosed herein may be used for the production of a wheat plant cultivar resistant to leaf rust disease, stripe rust disease or a combination thereof. According to certain embodiments, the resistance-conferring nucleic acid is introduced into a susceptible wheat cultivar, typically a cultivar suitable for commercial growth. According to the teachings of the present invention, said nucleic acid sequence is derived from a resistant *Ae. sharonensis* donor plant. According to some exemplary embodiment, the donor plant is AES accession No. TH548. Other related AES plants that exhibit resistance to the fungal disease leaf rust, stripe rust or combination thereof and identified using the DNA markers associated with the resistance as described herein, can also be used as resistance donors.

The resistance conferring nucleic acid sequence may be transferred to a recipient wheat plant by any method as is known to a person skilled in the art. According to certain embodiments, the AES nucleic acid sequence can be introduced by crossing the AES donor with the recipient wheat (i.e. by introgression) or by a doubled haploid technique. Alternatively, isolated AES nucleic acid sequence can be introduced as described hereinbelow. Transformation is optionally followed by selection of offspring plants comprising the resistance-conferring sequence and exhibiting resistance to at least one of the fungal disease stripe rust and leaf rust.

The resistance-conferring nucleic acid sequence may be isolated from an AES donor plant by using any method as is known in the art.

Transforming plants with isolated nucleic acid sequence generally involves the construction of an expression vector that will function in plant cells. According to the teachings of the present invention, such a vector comprises a nucleic acid sequence that comprises a segment of *Ae. sharonensis* chromosome $6S^{sh}$ that confers resistance to a disease selected from the group consisting of leaf rust, stripe rust or a combination thereof. Typically, the vector comprises the resistance-conferring gene(s) under control of or operatively linked to a regulatory element. According to certain embodiments, the regulatory element is selected from the group consisting of a promoter, and enhancer and a translation termination sequence. The expression vector may contain one or more such operably linked gene/regulatory element combinations, provided that at least one of the genes contained in the combinations encodes for the disease resistance. The vector(s) may be in the form of a plasmid, and can be used, alone or in combination with other plasmids, in a method for producing transgenic plants that are resistant to a disease selected from the group consisting of leaf rust, stripe rust or a combination thereof, using transformation methods known in the art to be suitable for transforming nucleic acid sequences into wheat (monocotyledonous) plants.

Expression vectors can include at least one marker (reporter) gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the markers gene). Many commonly used selectable marker genes for plant transformation are known in the art, and include, for example, genes that code for enzymes that metabolically detoxify a selective chemical agent which may be an antibiotic or a herbicide, or genes that encode an altered target which is insensitive to the inhibitor. Several positive selection methods are known in the art, such as mannose selection. Alternatively, marker-less transformation can be used to obtain plants without mentioned marker genes, the techniques for which are known in the art.

Methods for transforming a plant cell with nucleic acids sequences according to the present invention are known in the art. As used herein the term "transformation" or "transforming" describes a process by which a foreign nucleic acid sequence, such as a vector, enters and changes a recipient cell into a transformed, genetically modified or transgenic cell. Transformation may be stable, wherein the nucleic acid sequence is integrated into the plant genome and as such represents a stable and inherited trait, or transient, wherein the nucleic acid sequence is expressed by the cell transformed but is not integrated into the genome, and as such represents a transient trait. According to typical embodiments the nucleic acid sequence of the present invention is stably transformed into a plant cell.

There are various methods of introducing foreign genes into both monocotyledonous and dicotyledonous plants (for example, Potrykus I. 1991. Annu Rev Plant Physiol Plant Mol Biol 42:205-225; Shimamoto K. et al., 1989. Nature 338:274-276).

The principal methods of the stable integration of exogenous DNA into plant genomic DNA includes two main approaches:

*Agrobacterium*-mediated gene transfer: The *Agrobacterium*-mediated system includes the use of plasmid vectors that contain defined DNA segments which integrate into the plant genomic DNA. Methods of inoculation of the plant tissue vary depending upon the plant species and the *Agrobacterium* delivery system. A widely used approach is the leaf-disc procedure, which can be performed with any tissue explant that provides a good source for initiation of whole-plant differentiation (Horsch et al., 1988. Plant Molecular Biology Manual A5, 1-9, Kluwer Academic Publishers, Dordrecht). A supplementary approach employs the *Agrobacterium* delivery system in combination with vacuum infiltration. *Agrobacterium* mediated transformation protocols for wheat are known to a person skilled in the art.

Direct nucleic acid transfer: There are various methods of direct nucleic acid transfer into plant cells. In electroporation, protoplasts are briefly exposed to a strong electric field, opening up mini-pores to allow DNA to enter. In microinjection, the nucleic acid is mechanically injected directly into the cells using micropipettes. In microparticle bombardment, the nucleic acid is adsorbed on microprojectiles such as magnesium sulfate crystals or tungsten particles, and the microprojectiles are physically accelerated into cells or plant tissues. Another method for introducing nucleic acids to plants is via the sonication of target cells. Alternatively, liposome or spheroplast fusion has been used to introduce expression vectors into plants.

Following transformation of wheat target tissues, expression of the above described selectable marker genes allows for preferential selection of transformed cells, tissues and/or plants, using regeneration and selection methods now well known in the art.

Alternatively, the resistance-conferring AES chromosome segment may be transformed without prior isolation of the resistance-conferring nucleic acid sequence.

According to certain exemplary embodiments, the transfer of the AES chromosome segment is performed by introgression of the AES chromosome segment into a wheat cultivar, wherein the wheat cultivar is suitable for commercial growth.

According to certain embodiments, the method comprises the steps of:
a. providing a first wheat plant line susceptible to a rust disease, wherein the plant is a mutated plant homozygous to ph1 mutant gene and an *Ae. sharonensis* plant resistant to the rust disease;
b. crossing the first wheat plant line with the *Ae. sharonensis* plant to produce a first F1 progeny plants wherein the F1 plants are haploid hybrids;
c. crossing the first F1 progeny plants with a second wheat plant line homozygous for Gc2 mutation and carrying a normal Ph1 allele.
d. selecting progeny plants resistant to the at least one rust disease;
e. crossing the resistant progeny plants with an elite wheat plant cultivar susceptible to said at least one rust disease to produce a second F1 progeny;
f. backcrossing the second F1 progeny plants with the elite wheat plant cultivar to produce first backcross (BC1) progeny plants;
g. backcrossing the second F1 progeny plants with the elite wheat plant cultivar to produce first backcross (BC1) progeny plants;
h. selecting from the BC1 progeny plants that are self fertile and resistant to said at least one rust disease;
i. backcrossing the BC1 self fertile resistant plants with said elite cultivar plant at least twice to produced at least BC3 population;
j. selecting self fertile, resistant plants from the BC3 population;
k. selfing the plants of step (i) to produce BC3F2 population; and
l. selecting for non-segregating, self fertile resistant wheat plants resistant to said at least one rust disease and having a phenotype close to the phenotype of said elite cultivar plants.

It is to be explicitly understood that by selecting fully self fertile plants, the selection inherently encompasses selecting plants devoid of or heterozygous of the Gc2 gene.

Selecting resistant plant throughout the steps of the above-described method can be performed using phenotypic responses upon inoculation or alternatively employing marker-assisted selection using AES-markers as described herein. Quantitative or qualitative assessment of resistance to stripe rust or leaf rust caused by the fungus *Puccinia* can be performed as described in the Example section hereinbelow and as is known in the art. Combination of both methods may also be employed.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Material and Methods
Plant and Pathogen Material

Sharon goatgrass (*Ae. sharonensis*) Accession TH548 was collected in Palmahim, Israel (about 15 Km south of Tel Aviv; Millet E. et al., 2006. Isr. J. Pl. Sci. 54:243-248) and selected because of its seedling resistance to inoculation with either stripe rust (isolate #5006 of *P. striiformis* Virulence/Avirulence formula Yr6,7,8,9,11,12,17,19,sk,18,A/Yr1,5,10,15,24,26,sp) or leaf rust (isolate #526-24 of *P. triticina* Virulence/Avirulence formula Lr1,3,24,26,10,18, 21,23, 15/Lr2a,2c,9,16,3ka,11,17,30). Both isolates represent highly virulent pathogen races.

The spring wheat cv. Galil was selected as the recipient parent. This cultivar is known for its high productivity on one hand and its susceptibility to the *Puccinia* pathogen races on the other hand.

The wheat ph1b mutant (Mph) in the genetic background of "Chinese Spring" (CS) cultivar was originally obtained from the late E. R. Sears of the University of Columbia, Missouri. CS is also susceptible to the above mentioned fungi isolates.

The wheat "anti-gametocidal" mutant (AG) was obtained courtesy of B. Friebe (Kansa State University, Manhatten, Kans.). This line, also having CS background, has a homoeologous distal translocation $4S^{sh}L$ of *Ae. sharonensis* into the wheat 4BL arm (designated T4BS.4BL-$4S^{sh}L$) carrying the Gc2 allele which was further mutated by ethyl methanesulfonate (EMS) (Gc2$^{mut}$; Friebe B et al, 2003). From heterozygous (Gc2$^{mut}$/Gc2) plants, the transmission of the chromosomes carrying these alleles is regular (random) rather than preferential, as for the chromosome with the native gametocidal Gc2 allele.

Gene Transfer Procedure

The gene transfer procedure is summarized in FIG. 1. In the year 2005 the wheat ph1b mutant Mph was pollinated by Sharon goatgrass accession TH548 and few seeds were obtained. Two seeds were germinated (expected genome BADS$^{sh}$) and developed into apparently self sterile plants. These plants were pollinated by the AG "anti-gametocidal mutant" and produced 10 seeds. Some spikes were also pollinated by cv. Galil due to lack of pollen of AG pollen and produced 12 seeds. Offspring of these crosses segregated for their reaction towards stripe rust isolate #5006; four seedlings from the cross with the AG mutant plant and 5 from the cross with Galil plant were classified as resistant (disease infection type (IT)=0; in a scale of 4 of Long D L and Kolmer J A. 1989. Phytopathology, 79:525-529) and were further grown. Each of these plants represents a different recombination event and was labeled by a recombinant line number. These plants were pollinated by the other parent (either cv. Galil or AG and yielded the $F_1$ generation.

Seedlings at $F_1$ generation were phenotyped inter alia based on their resistance to stripe rust isolate #5006 and leaf rust isolate #526-24. Out of 55 seedlings tested, two seedlings were found resistant to both diseases; 10 seedlings were resistant only to stripe rust; and 3 seedlings were resistant only to leaf rust.

Resistant plants were used in 4 more backcrosses (BC) to cv. Galil as recurrent parent. Each generation was accompanied by seedling test of resistance/susceptibility to the pathogen for which the $F_1$ recombinant line was resistant. Seedlings were selected based on their resistance as well as on agronomic appearance and spike fertility. Selecting only plants with fertile spikes ensure that the selected plants are devoid of the gametocidal gene (Gc2). Agronomic appearance included at least one of erect growth habit, early heading, short stature and square-head non shattering spike.

At $BC_3$ and $BC_4$, progenies of resistant plants were allowed also to self pollinate. Resistant $F_2$ seedlings were selected and 20 of their $F_3$ seeds were phenotyped. $BC_3F_3$ and $BC_4F_3$ families having only resistant seedlings were considered as being homozygous resistant.

Evaluation of Seedling Resistance
Leaf Rust and Stripe Rust Inoculation and Evaluation Tests in Israel Seedlings of each generation were tested and selected for leaf rust and stripe rust resistance. Plants were sown and grown in small pots in a temperature controlled greenhouse at 22±2° C. Seven to 10 days after planting, seedlings were inoculated with a suspension of leaf rust or stripe rust urediniospores in a lightweight mineral oil (Soltrol 170). After the oil on the inoculated plants was allowed to evaporate, the plants were incubated overnight in a dew chamber at 18° C. for leaf rust and 9° C. for 16 hours in dark followed by 15° C. in light for stripe rust.

Leaf rust-inoculated plants were kept for 12-14 days in the greenhouse and were scored for infection type (IT) on a standard scale of 0 (highly resistant) to 4 (highly susceptible). ITs of 0 to 2 were considered indicative of a resistant response and 3 to 4 as a susceptible response.

Stripe rust-inoculated plants remained in a 15° C. growth chamber with 12 h light, 12 h dark regime for 14 to 17 days, after which ITs were scored using the same scale used for leaf rust.

Stripe Rust Inoculation and Evaluation Tests in Pullman, Wash.

The AES-wheat recombinant lines were tested for reaction to stripe rust at the seedling stage under controlled conditions following the procedure described by Chen X M and Line R F. 1992. Phytopathology, 82:633-637). Four races of *P. striiformis f.* sp. *tritici*, PST-43, PST-100, PST-114, and PST-127 which collectively cover all virulence factors identified thus far in the U.S. and represent predominant races (Chen X M. 2005. Can. J. Plant Pathol. 27:314-337; Chen X M et al., 2010 Can. J. Plant Pathol. 32:315-333), were used in the tests. Seedlings at the two-leaf stage were inoculated with a mixture of fresh urediniospores and talc (Sigma, St. Louis, Mo., USA) at a 1:20 ratio. The inoculated plants were incubated for 24 h in a dew chamber at 10° C. without light, and then moved to a growth chamber under a diurnal temperature cycle gradually changing from 4° C. at 2:00 AM to 20° C. at 2:00 PM with a 16 h light/8 h dark cycle. About 20 to 22 days after inoculation, the infection types of each plant were recorded using a 0-9 scale with 0 indicating no visible symptoms and 9-highly susceptible (Line R F and Qayoum A. 1992. U.S. Department of Agriculture Technical Bulletin No. 1788, pp. 44).

Leaf Rust Inoculation and Evaluation Tests in St. Paul, Minn.

To further characterize the resistance spectrum of AES lines for possible use in US breeding programs, an additional leaf rust resistance test was made with race TFBJQ (isolate US1-1) of *P. triticina*. Race TFBJQ is unique in that it possesses virulence for Lr21, a resistance gene widely used in hard red spring wheat cultivars in the U.S.A. and now rendered ineffective with the appearance of Lr21-virulent *P. triticina* isolates. Seedlings of the AES-wheat recombinant lines and controls were inoculated with urediniospores of race TFBJQ suspended in a lightweight mineral oil (approximately 0.014 mg of spores per plant). Following inoculation, plants were transferred to mist chambers and incubated for 16 h in darkness at 18 to 21° C. and approximately 100% relative humidity (RH). After the mist period, plants were allowed to dry for 4 h before being placed in a growth chamber at 18 to 21° C. with a 14-h photoperiod (14 h light/10 h dark cycle). Twelve days after inoculation, plants were evaluated for their infection types based on the 0 to 4 scale of Long and Kolmer (1989, ibid).

DNA Extraction

DNA was extracted from 4-5 putatively homozygous $BC_4F_3$ plants of 4 lines (5 genotypes, two belonging to the same line) that were initially selected for their leaf rust resistance (RL lines) and 4 lines (5 genotypes) that were initially selected for their stripe rust resistance (RY lines).

High-quality genomic DNA was extracted from 0.3-0.5 g of freeze-dried leaf tissue from young leaves using a modified cetyl-trimethyl-ammonium bromide (CTAB) method of Doyle, J J and J L Doyle (1987. *Phytochemistry Bulletin* 19:11-15). Plant material was ground in a Tissue-lyser (Geno/Grinder) with 1 ml CTAB extraction buffer containing 41.7% extraction buffer (0.35M sorbitol, 0.1M Tris HCl and 5Mm EDTA), 41.7% lysis buffer (0.2M Tris HCl, 0.05M EDTA, 2M NaCl and 2% CTAB), 16.7% Sarcosyl (5%), 0.5% Sodium-bisulfite and 2% PVP-40 preheated to 65° C.

Samples were incubated at 65° C. for 1 hour with occasional gentle swirling and de-proteinized with 0.8 ml of chloroform/isoamylalcohol (24:1). The resulting mixture was vigorously shaken for 15 min and then centrifuged at 10,000 g for 20 min. DNA was precipitated from the aqueous phase by adding 1 ml of ice-cold isopropanol and mixing by gently inverting the tubes. The tubes were stored at −20° C. overnight and then centrifuged at 10000 g for 30 min. The DNA pellet was washed with 70% ethanol, dried, and finally dissolved in 250 μl of 1×TE (10 mM Tris HCl, 1 mM EDTA) by overnight incubation at room temperature.

DNA quality was examined on a 0.8% agarose gel and quantified using a NanoDrop spectrophotometer (Maestrogen Inc., Las Vegas Nev., USA). The concentration of DNA in the samples was adjusted to 50-70 ng/ul and the samples were stored at −20 C. Samples were shipped to Diversity Arrays Technology Pty. Ltd. (Yarralumla, Australia) following the company instructions.

DArT Analysis

About 1000 wheat markers, but only few (out of about 1000) *Ae. sharonensis* markers were mapped on chromosomes by DArT Pty. Ltd. Additional mapping data on AES markers were gratefully obtained from M. Moscou, the Sainsbury Laboratory, John Innes Centre, Norwich UK. These consensus map data were produced from three segregating AES populations. The markers were assembled into linkage groups with the aid of SNP data (M. Moscou—personal communication). In a number of cases, polymorphisms existed between AES and the wheat cv. Galil, but not between AES and wheat cv. CS.

Map Drawing

Polymorphic DArT markers with known map location and linkage groups (segments) were plotted using MapChart 2.2 software (Voorrips 2002. J. Hered. 93:77-78). Three cases of marker substitution were considered: absence of a wheat (Galil and CS) marker in the recombinant lines; absence of a wheat marker in a recombinant line and in CS, but not in Galil (which prevents an unequivocal determination that AES chromatin substitutes for wheat chromatin); and presence of an AES (aePt) or a wheat (wPt) marker in a recombinant line only, but not in the wheat parents (Galil and CS). The different linkage groups that were defined herein (FIG. 2 and FIG. 3) in order to increase map resolution do not necessarily reflect the complete chromosome constitution due to large gaps between markers in certain regions.

Example 1: Production of the Introgression Lines

By induction of homoeologous pairing using the gene transfer procedure described hereinabove a number of $BC_4F_3$ introgression lines homozygous resistant for certain pathotypes of leaf rust and/or yellow (stripe) rust causing fungi were obtained. The lines have agronomic appearance, resemble their recurrent parent cv. Galil and are self fertile. The lines can be used in breeding programs to improve wheat resistance to these diseases.

Example 2: Leaf Rust Resistant Lines

One $BC_4$ leaf rust resistant line, RL-17, was derived from pollination of the haploid hybrid ($F_1$ Mph×AES) by the AG mutant. This line is characterized by large AES segment(s) spanning together the whole 6B chromosome. Nevertheless, two Galil markers were still present at positions 12.7 and 54.3 (chromotype a; FIG. 2). Three other leaf rust resistant lines (RL-76, RL-86 and RL-510) were derived from a cross of the haploid hybrid with cv. Galil before its offspring were pollinated by the AG mutant. All of these 3 lines had a similar short intercalary AES region of 22 cM on chromosome 6B; RL-510 being different from the two other lines by the absence of a couple of wheat markers at 50.6 cM (chromotypes b and c). Yet, within this region, two segments of Galil markers were found (ca. 30-38 cM and 47-50 cM). However, only three AES markers, namely aePt947170 (having the nucleic acid sequence set forth IN SEQ ID NO:1), aePt948067 and tPt0910 (having the nucleic acid sequence set forth IN SEQ ID NO:2) mapping to 38.5, 38.9 and 41.5 cM, respectively, were found in common with all of the recombinant chromotypes. This suggests that these AES markers are linked to the leaf rust resistance gene. All of these RL lines were consistently highly resistant to leaf rust isolate #526-24.

Example 3: Stripe Rust Resistance Lines

All of the $BC_4$ stripe rust resistant lines were derived from pollination of the haploid hybrid ($F_1$ Mph×AES) by the AG mutant followed by pollination of the offspring by cv. Galil. The chromosome constitution of lines RY-32-3-3 and RY-41 was similar to that of line RL-17 (AES segment(s) spanning the whole 6B chromosome with only 2 Galil markers; chromotype d, FIG. 3). Line RL32-3-14 had also long AES insertion (about 74 cM) but its telomeres were typically of Galil type. The two other lines showed a similar chromotypes (f and g). They both had an intercalary AES region between 38.5 and 48 cM followed by another region from 48 to 87 cM of mosaics of wheat and AES markers. Several distinct AES markers were common to all recombinant chromotypes: aePt947170 (mapped on 38.5 cM, having the nucleic acid sequence set forth IN SEQ ID NO:1), tPt0910 (41.5 cM, having the nucleic acid sequence set forth IN SEQ ID NO:2) aePt948252 (62.1 cM), aePt948565 and aePt947177 (66.5 cM) and aePt949079 (86.8 cM). It is noteworthy that only aePt947170 and tPt0910 were common to all the RL chromotypes too. All of these lines were consistently highly resistant to stripe rust isolate #5006.

Example 4: Resistance of Lines to North American Races of *P. striiformis* f. Sp. *Tritici*

Five homozygous stripe rust resistant $BC_3F_4$ lines (RY lines) and 3 leaf rust resistant $BC_3F_4$ lines (RL lines) were phenotyped in 2007 for their reaction against four North American races of the stripe rust pathogen in Pullman, Wash. Races Pst-43, Pst-100, Pst-114, and Pst-127 of *Puccinia striiformis* f sp. *tritici* were examined at the plant seedling stage under controlled greenhouse condition. The results are given in Table 1.

Example 5: Resistance of the Lines to North American Leaf Rust

Three homozygous $BC_3F_4$ lines (RL lines) that were originally selected for the resistance to the Israeli leaf rust isolate 526-24 were examined for their reaction to the American leaf rust race TFBJQ having Lr21 virulence in St. Paul, Minn., 2012. The results are given in Table 2.

TABLE 2

Reaction of three $BC_3F_4$ lines resistant to leaf rust isolate 526-24 to leaf rust races having Lr21 virulence

| Line | Infection type* | General Reaction** | Comment |
|---|---|---|---|
| Galil wheat | 3 plant = 2 to 3 −/<br>1 plant = 2 to 1 | MS-MR | Some variation in the reactions |
| RL-17-1-3 | 3 plants = 1=<br>1 plant = 0; 1−<br>1 plant = 2 to 3−<br>1 plant = 3 | R<br>R<br>MS<br>R | Clear and extreme segregation for infection types |
| RL-17-1-9 | 8 plants = 0; to 0; 1= | HR to R | Minor variation in infection types |

TABLE 1

Infection type (IT) of *Aegilops sharonensis*-wheat translocation lines infected with races of *Puccinia striiformis* f. sp. *tritici*

| | | Infection type* (No. of plants) by PST races** | | | |
|---|---|---|---|---|---|
| Line | Selected for Resistance to | PST-43 | PST-100 | PST-114 | PST-127 |
| Galil Wheat (A) | Parental line | 1 (5) | 1 (4), 3 (1) | 8 (5) | 2, 3 (5) |
| Galil Wheat (B) | Parental line | 1 (5) | 1 (3), 8 (2) | 8 (5) | 1 (3), 3 (1) |
| RL-17-1-3 | Leaf rust | 1 (5) | 1-2 (5) | 7 (3), 2 (2) | 1 (3), 3 (2) |
| RL-17-1-9 | Leaf rust | 1 (5) | 1 (4) | 7 (3), 2 (2) | 1 (5) |
| RL-610-5-5 | Leaf rust | 1 (4) | 1 (4) | 7 (3), 2 (2) | 1 (5) |
| RY-24-4-2 | Stripe rust | 1 (5) | 1 (5) | 3, 4 (5) | 1 (5) |
| RY-32-1-1 | Stripe rust | 1 (5) | 1 (4) | 2 (5) | 1 (5) |
| RY-41-6-2 | Stripe rust | 1 (5) | 1-2 (4) | 2, 3 (5) | 1 (5) |
| RY-6-37-1 | Stripe rust | 1 (5) | 1 (5) | 2 (5) | 1 (5) |
| RY-74-4-3 | Stripe rust | 2 (5) | 1 (5) | 2, 3 (5) | 1 (5) |
| Lemhi | (susceptible control) | 8 (5) | 8 (6) | 8 (5) | 8 (5) |

*Infection type was recorded 21 days after inoculation.
The virulence formula of the tested races on US differentials* are: Pst-43: 1, 3, 4, 5, 12, 14 Pst-100: 1, 3, 8, 9, 10, 11, 12, 16, 17, 18, 19, 20 Pst-114: 1, 3, 8, 9, 10, 11, 12, 14, 16, 17, 18, 19, 20 Pst-127: 1, 2, 3, 5, 6, 8, 9, 10, 11, 12, 13, 15, 16, 17, 18, 19, 20
***US differentials: 1 = Lemhi (Yr21), 2 = Chines 166 (Yr1), 3 = Heines VII (Yr2, YrHVII), 4 = Moro (Yr10, YrMor), 5 = Paha (YrPa1, YrPa2, YrPa3), 6 = Druchamp (Yr3a, YrD, YrDru), 7 = AvSYr5NIL (Yr5), 8 = Produra (YrPr1, YrPr2), 9 = Stephens (Yr3a, YrS, YrSte), 10 = Yamhill (Yr2, Yr4a, YrYam), 11 = Lee (Yr7, Yr22, Yr23), 12 = Fielder (Yr6, Yr20), 13 = Tyee (YrTye), 14 = Tres (YrTr1, YrTr2), 15 = Hyak (Yr17, YrTye), 16 = Express (YrExp1, YrExp2), 17 = AvSYr8NIL (Yr8), 18 = AvSYr9NIL (Yr9), 19 = Clement (Yr9, YrCle), and 20 = Compair (Yr8, Yr19).

As is apparent from Table 1, resistance of Galil to all PST races except Pst114 masked the reaction of the recombinant lines to these races. However, Galil wheat was highly susceptible to PST-114. All the lines selected to be resistant to yellow rust (RY lines) were resistant to PST-114. Most of the lines showed IT 2, with line no 24-4-2 showing IT 4 on the 0-9 scale. The five seedlings of each of the three leaf rust resistant lines (RL) segregated into 3 resistant and 2 susceptible individuals in response to stripe rust PST-114.

Race-PST114 was first detected in Washington State in 2004 and was one of the top predominant races in the US from 2005 to 2009. It appears at high frequency throughout the country, but is mostly restricted to the US Pacific Northwest area (Washington, Idaho, Oregon, and western Montana). The major characteristic of PCT-114 is its combination of virulence to Yr10, Yr8 and Yr9.

TABLE 2-continued

Reaction of three $BC_3F_4$ lines resistant to leaf rust isolate 526-24 to leaf rust races having Lr21 virulence

| Line | Infection type* | General Reaction** | Comment |
|---|---|---|---|
| RL-610-5-3 | 8 plants = 0; to 0; 1= | HR to R | Minor variation in infection types |
| Little Club | 8 plant = 4 | S | Consistently high infection types |

S—Susceptible;
R—resistant;
MS—moderate susceptibility;
HR—Highly resistant.
*Infection types scored according to a 0-4 scale. Minus (−) and double minus (=) notations indicate reduced and highly reduced sporulation of uredinia, respectively, compared to classically described infection types.
**General reactions were as follows: 0 to 0; = Highly Resistant; 0; 1 to 1 to 2 = Resistant; 2 to 1 = Moderately Resistant; 2 to 3− = Moderately Susceptible; and 3− to 4 = Susceptible.

Galil wheat expressed reactions ranging from moderate susceptibility to moderate resistance to L21 virulent isolate. Hence its genetic background may mask the reaction of the introgression lines. Even so, two of the lines selected to be resistant to leaf rust (RL-17-1-9 and RL-610-5-3) exhibited high resistance response. One line (171-3) segregated for the response.

Lr21 is present in 50% of the acreage of hard red spring wheat in North Dakota and Minnesota. If not treated, it causes an epidemic disease.

Example 6: Genome Analysis—DArT Analysis

As mentioned above, DArT analysis revealed alien introgressions almost exclusively on wheat chromosome 6B while there was no indication for alien segment introgression in other chromosomes. There were only few instances of single alien markers across the wheat genome, but these were not found consistently in all of the plants of a line. This indicates an efficient recovery of the wheat genetic background.

Using the DArT marker consensus map data obtained from A. Kilian, (DArT Pty. Ltd.), 67 wheat markers that were used in this study were mapped on chromosome 6B but cv. Galil had only 38 markers. These markers were indicative of the presence of Galil chromatin and their absence served as indication of alien substitution. In addition, using the DArT AES map provided by courtesy of M. Moscou (unpublished), 18 aePt markers on chromosome $6^{sh}$ of AES were informative. The markers were not evenly distributed and tended to concentrate between the short arm telomere (distance 0) and 16.4 cM and then between 30 and 71 cM (FIGS. 2 and 3). In many cases, more than one marker was mapped to the same position.

It is noteworthy that several regions of the chromosome are not saturated with markers and it is possible that the mentioned segments can be further split into shorter sub segments.

Example 7: Reduction of the Introgression Size

A resistant BC4F4 wheat-AES introgression line is crossed to the ph1b mutant wheat line. $F_1$ plants are backcrossed to the ph1b mutant and homozygous ph1b plants are selected by molecular markers. Homoeologous pairing occur in these plants and they are hybridizing with cv. Galil to produce hybrid F1 plants. These F1 plants are selected for their resistance to the pathogen and F2 seedlings are phenotyped against the pathogen and susceptible plants discarded. F2:3 seedling reaction to the pathogens are used to select homozygous resistant progenies. DArT markers and additional marker as are known in the art are then used to select offspring with a small alien segment. Selected homozygous $F_2$ are backcrossed to the wheat parental cultivar. This step is accompanied by phenotyping against selected Israeli and North American races of the *Puccinia* pathogen. Secondary recombinants that carry the gene in different locations, for example a secondary recombinant with a proximal alien segment and another with a distal alien segment, are intercrossed to allow for pairing in the overlapping alien chromosomal region thus to further reduce the alien segment size.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A wheat cultivar suitable for commercial growth comprising within the central part of chromosome 6B a genetic element comprising a segment of chromosome 6S$^{sh}$ of *Aegilops sharonensis* Accession TH548, seed of which have been deposited with NCIMB Ltd. as the International Depositary Authority under Accession No. NCIMB 43567, the segment ranging from position 30 cM to position 70 cM and comprising at least one marker selected from the group consisting of aePt947170 mapped on 38.5 cM and having the nucleic acid sequence set forth in SEQ ID NO: 1, tPt0910 mapped on 41.5 cM and having the nucleic acid sequence set forth in SEQ ID NO:2, and a combination thereof, wherein Ae. Sharonensis segment confers or enhances resistance of the wheat cultivar to a disease selected from the group consisting of leaf rust, stripe rust, and a combination thereof.

2. The wheat cultivar of claim 1, wherein the segment of *Ae. sharonensis* chromosome 6S$^{sh}$ confers resistance to leaf rust disease, said segment further comprises the marker aePt948067 mapped on 38.9 cM.

3. The wheat cultivar of claim 1, wherein the segment of *Ae. sharonensis* chromosome 6S$^{sh}$ confers resistance to stripe rust disease, said segment further comprises at least one additional marker selected from the group consisting of aePt948252 mapped on 62.1 cM, aePt948565, aePt947177 mapped on 66.5 cM, and any combination thereof.

4. The wheat cultivar of claim 1, wherein the segment of *Ae. sharonensis* chromosome 6S$^{sh}$ confers resistance to leaf rust disease and stripe rust disease, said segment comprises the markers aePt947170 (mapped on 38.5 cM and having the nucleic acid sequence set forth in SEQ ID NO: 1 and tPt0910 mapped on 41.5 cM and having the nucleic acid sequence set forth in SEQ ID NO:2.

5. The wheat cultivar of claim 1, said cultivar is selected from an inbred plant homozygous for the chromosome 6B comprising the segment of *Ae. sharonensis* chromosome 6S$^{sh}$ and a hybrid heterozygous plant comprising the native wheat chromosome 6B and chromosome 6B comprising the segment of *Ae. sharonensis* chromosome 6S$^{th}$.

6. The wheat cultivar of claim 1, said cultivar is resistant to leaf rust disease and stripe rust disease.

7. The wheat cultivar of claim 1, said cultivar is devoid of at least one of ph1 mutant alleles and *Ae. Sharonensis* gametocidal Gc2 gene and/or a mutant thereof.

8. The wheat cultivar of claim 1, wherein the leaf rust disease is caused by the fungus *Puccinia triticina* and wherein the stripe rust disease is caused by the fungus *Puccinia striiformis*.

9. A seed of the wheat cultivar of claim 1, wherein a plant grown from the seed comprises within the central part of chromosome 6B a genetic element comprising a segment of chromosome 6S$^{sh}$ of *Aegilops sharonensis* Accession TI-1548, seed of which have been deposited with NCIMB Ltd. as the International Depositary Authority under Accession No. NCIMB 43567, the segment ranging from position 30 cM to position 70 cM and comprising at least one marker selected from the group consisting of aePt947170 mapped on 38.5 cM and having the nucleic acid sequence set forth in SEQ ID NO:1, tPt0910 mapped on 41.5 cM and having the nucleic acid sequence set forth in SEQ ID NO:2, and a combination thereof, wherein the chromosome segment conferring or enhancing resistance of the grown wheat plant to a disease selected from the group consisting of leaf rust, stripe rust and a combination thereof.

10. A cell or a tissue culture obtained from the plant of claim 1, wherein a plant developed from the cell or tissue comprises within the central part of chromosome 6B a genetic element comprising a segment of chromosome 6S$^{sh}$ of *Aegilops sharonensis* Accession TH548, seed of which have been deposited with NCIMB Ltd. as the International Depositary Authority under Accession No. NCIMB, the segment ranging from position 30 cM to position 70 cM and comprising at least one marker selected from the group consisting of aePt947170 mapped on 38.5 cM and having the nucleic acid sequence set forth in SEQ ID NO: 1, tPt0910 mapped on 41.5 cM and having the nucleic acid sequence set forth in SEQ ID NO:2, and a combination thereof, wherein the chromosome segment confers or enhances resistance of the developed wheat plant to a disease selected from the group consisting of leaf rust, stripe rust, and a combination thereof.

11. A method for producing a wheat cultivar resistant to at least one rust disease, the method comprises introducing into the central part of chromosome 6B of a wheat cultivar susceptible to the disease a genetic element comprising a segment of chromosome 6S$^{sh}$ of *Aegilops sharonensis* Accession TH548, seed of which have been deposited with NCIMB Ltd. as the International Depositary Authority under Accession No. NCIMB, the segment ranging from position 30 cM to position 70 cM and comprising at least one marker selected from the group consisting of aePt947170 mapped on 38.5 cM and having the nucleic acid sequence set forth in SEQ ID NO:14, tPt0910 mapped on 41.5 cM and having the nucleic acid sequence set forth in SEQ ID NO:2, and a combination thereof, wherein said segment comprises at least one locus conferring resistance to at least one of leaf rust disease, stripe rust disease, and a combination thereof, thereby producing a wheat cultivar resistant to said at least one rust disease.

12. The method of claim 11, wherein the segment of *Ae. sharonensis* chromosome 6S$^{sh}$ confers resistance to leaf rust disease, said segment further comprises the marker aePt948067 mapped on 38.9 cM.

13. The method of claim 11, wherein the segment of *Ae. sharonensis* chromosome 6S$^{sh}$ confers resistance to stripe rust disease, said segment further comprises the at least one additional marker selected from the group consisting of aePt948252 (mapped on 62.1 cM, aePt948565, aePt947177 mapped on 66.5 cM, and any combination thereof.

14. The method of claim 11, wherein the segment of *Ae. sharonensis* chromosome 6S$^{sh}$ confers resistance to leaf rust disease and stripe rust disease, said segment comprises the markers aePt947170 mapped on 38.5 cM and having the nucleic acid sequence set forth in SEQ ID NO:1 and tPt0910 mapped on 41.5 cM and having the nucleic acid sequence set forth in SEQ ID NO:2.

15. The method of claim 11, wherein the produced wheat cultivar is resistant to leaf rust disease and stripe rust disease.

16. The method of claim 11, wherein the leaf rust disease is caused by the fungus *Puccinia triticina* and wherein the stripe rust disease is caused by the fungus *Puccinia striiformis*.

17. A method for producing a wheat cultivar resistant to at least one disease caused by the fungus *Puccinia*, the method comprises introducing into the central part of chromosome 6B of a wheat cultivar susceptible to the disease a genetic element comprising a segment of chromosome 6S$^{sh}$ of *Aegilops sharonensis*, Accession TH548, seed of which have been deposited with NCIIIB Ltd. as the International Depositary Authority under Accession No. NCIMB, the segment ranging from position 30 cM to position 70 cM and comprising at least one marker selected from the group consisting of aePt947170 mapped on 38.5 cM and having the nucleic acid sequence set forth in SEQ ID NO: 1, tPt0910 mapped on 41.5 cM and having the nucleic acid sequence set forth in SEQ ID NO:24, and a combination thereof, thereby producing a wheat cultivar resistant to said at least one disease, which is selected from the group consisting of leaf rust, stripe rust and a combination thereof.

* * * * *

SEQUENCE LISTING

<160> NUMBER OF SEQ ID NOS: 2

<210> SEQ ID NO 1
<211> LENGTH: 608
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Marker Sequence

<400> SEQUENCE: 1

```
tggtgtctgt atcatctagt cttttcagtt ttagttcacc attggttgtc ttaaccattt      60
ctgctacctt tggtattcgg gttgtgacta taatcaaatt accctgagac tctaccttct     120
ttaaaggtgt tattagtttt ttccactcat cctcctgata tgtccacaca tcatccaaga     180
caagtaaaaa cctcttacct tttaatcttt gttggataag ttcttcggca ctagcgttaa     240
ccttttcacc aacaacacta tcgatttttt ttactatctc ttgtgccaac ctatctgcac     300
tgaaatcgaa agagacacat atccaaattg aagcctggaa gtagctactc acttcttggc     360
atatgtgttg cgtaaaagtt gtttttccaa tacccccgg tccaaaaatt ggaagcacgt     420
taagtttatt gggacagtac tcgcgactaa taatgcaatc tacaattttc ttttttggt     480
```

```
catccctccc atataactca ggttctataa tctctgatgt ggtctttgat ctgtttttg      540 caatttcttt ggtatggtta cggctggaac ccaacaaatc tagattaaga attatggaga    600
ccttagca                                                              608
```

<210> SEQ ID NO 2
<211> LENGTH: 625
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Marker Sequence

<400> SEQUENCE: 2

```
tgcagcggtg agaagagcga acaatggagc ctccagcttt attacctacg acgacatctc     60
caagctcaag tacactgcta aggtactaaa gtacaaacat tttttacag taaggaagct    120 gaggcccggc gttaaatcag tgatgcgttt acagagaaca acacaacatg ccgccacaca    180
tgacctgaaa acgaaactgc aaaggaaaac tcatcaccaa tgacattcta tatattccaa    240
ctttcacttc agtatgtaaa actaacttgg attacttata ttgttttttgg attttgtaatc  300 aatgacacca tatgtaacaa aacatgtata tattactccc tccgttccca aatgtaagtc    360
tttgtagaaa tttcattata aactgcatac ggatgtatat agatgcattt taagtttaga    420
ttcattcatt ttgctcctta tgtagtccat ctagtgcaat ctctacaaag acttatattt    480
aggagcggag ggagtacgat gcaacatact gcaaggcggt gcccgatcaa cccctcctca    540
tatgcgaacc tggacgattt agctataaat gagttgtgtt agtctagtac attttgtaat    600
tcacttatct gtaccctaa ctgca                                           625
```